US010126297B2

(12) United States Patent
Chatterjee et al.

(10) Patent No.: US 10,126,297 B2
(45) Date of Patent: Nov. 13, 2018

(54) AUTOMATED DRIVING OF AN ASSAY

(71) Applicant: Fannin Innovation Studio, Inc., Houston, TX (US)

(72) Inventors: Dev Chatterjee, Saint Louis, MO (US); Leo Linbeck, III, Houston, TX (US); Michael John Heffernan, Katy, TX (US); Atul Varadhachary, Bellaire, TX (US)

(73) Assignee: Fannin Partners, LLC, Houston, TX (US)

( * ) Notice: Subject to any disclaimer, the term of this patent is extended or adjusted under 35 U.S.C. 154(b) by 0 days.

(21) Appl. No.: 15/793,445

(22) Filed: Oct. 25, 2017

(65) Prior Publication Data
US 2018/0113126 A1  Apr. 26, 2018

Related U.S. Application Data

(60) Provisional application No. 62/412,734, filed on Oct. 25, 2016.

(51) Int. Cl.
| | |
|---|---|
| *G01N 35/04* | (2006.01) |
| *G01N 33/543* | (2006.01) |
| *G01N 33/487* | (2006.01) |
| *H01F 7/121* | (2006.01) |
| *B01L 3/00* | (2006.01) |
| *H01F 7/06* | (2006.01) |
| *G01N 35/00* | (2006.01) |

(52) U.S. Cl.
CPC .... *G01N 33/54326* (2013.01); *B01L 3/50855* (2013.01); *B01L 3/502715* (2013.01); *G01N 33/48785* (2013.01); *G01N 33/54386* (2013.01); *G01N 35/0098* (2013.01); *H01F 7/064* (2013.01); *H01F 7/121* (2013.01); *G01N 2035/00574* (2013.01)

(58) Field of Classification Search
CPC combination set(s) only.
See application file for complete search history.

(56) References Cited

U.S. PATENT DOCUMENTS

| | | | | |
|---|---|---|---|---|
| 2009/0325274 | A1* | 12/2009 | Hamada | G01N 35/026 435/286.2 |
| 2013/0209334 | A1* | 8/2013 | Wilson | B01L 3/50825 422/554 |

* cited by examiner

*Primary Examiner* — Paul S Hyun
(74) *Attorney, Agent, or Firm* — Eric P. Mirabel

(57) ABSTRACT

The invention herein relates to conducting assays with an apparatus including a substantially transparent assay cartridge loaded with magnetic beads, and a magnet carrier base positioned below a scanning platform holding the assay cartridge. The assay cartridge includes magnetic beads, sample and control solutions in some wells, and assay reagents in others. A microcomputer controls a stepping motor which controls movement of the magnet carrier base, and causes the magnetic beads to travel from one well to another. An electromagnetic coil-spring assembly induces mixing of well contents with the magnetic beads on actuation. The assay cartridge is authenticated by sending its encoded identifier to a server or website, and assay instructions are provided remotely to the microcomputer. Following assay completion, the cartridge can have color change or other assay indication detected, and the results sent to the server or website or another recipient.

25 Claims, 30 Drawing Sheets

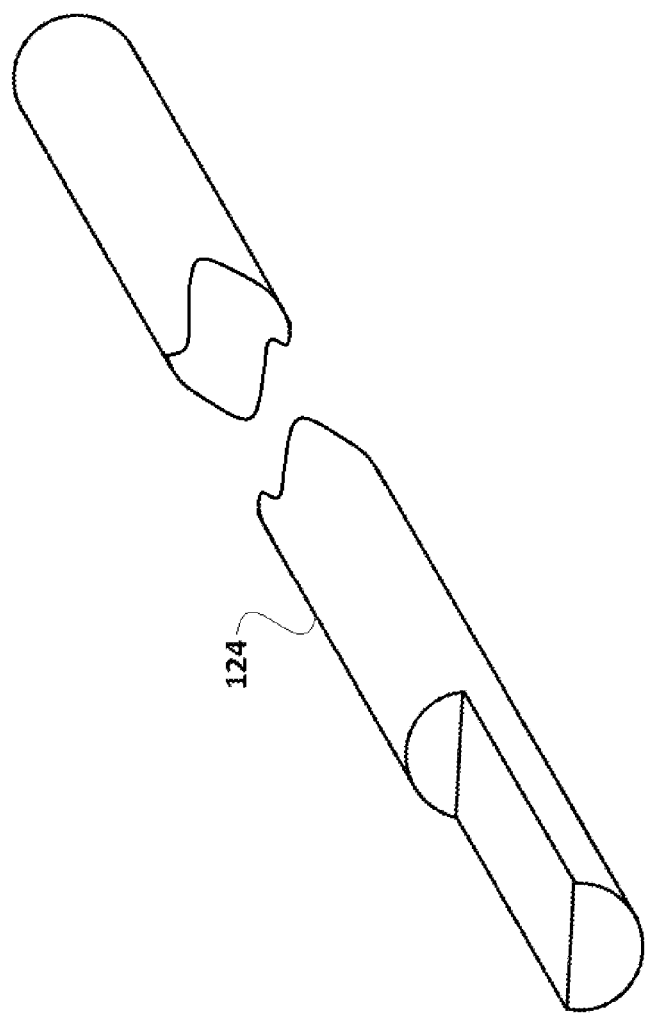

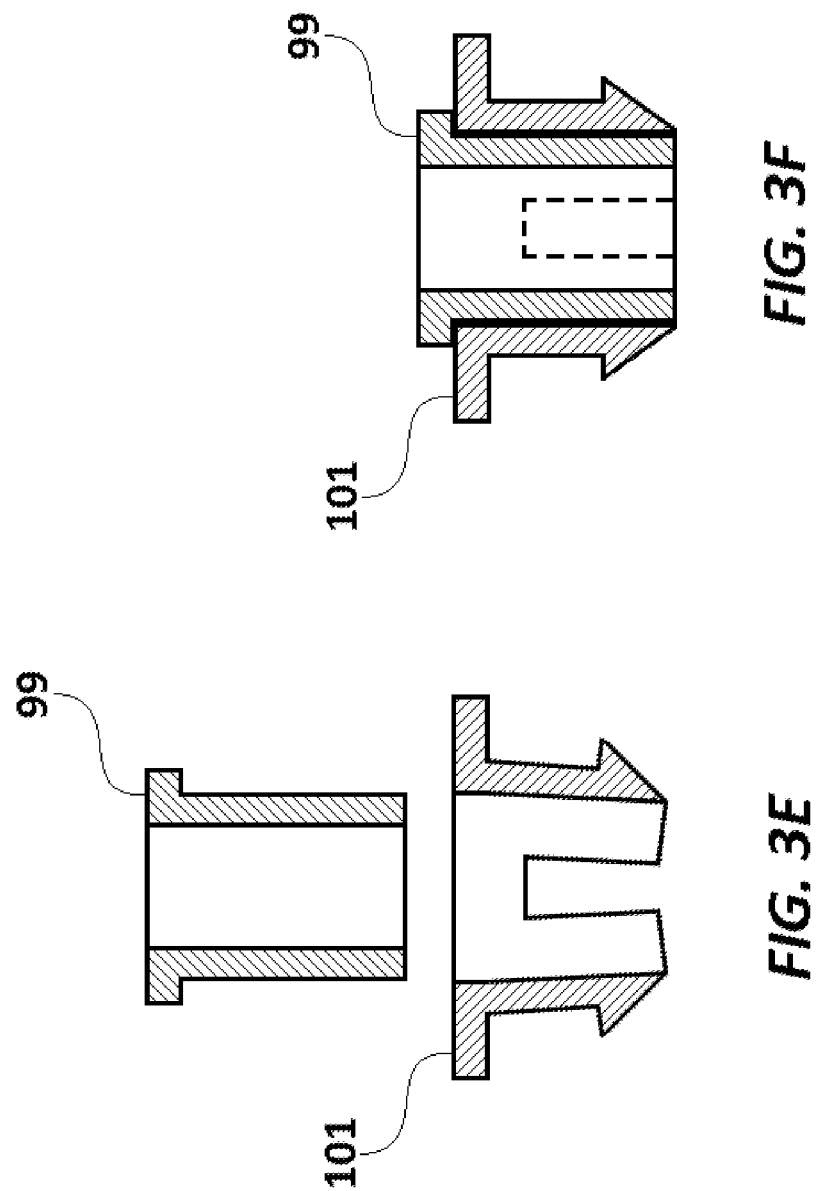

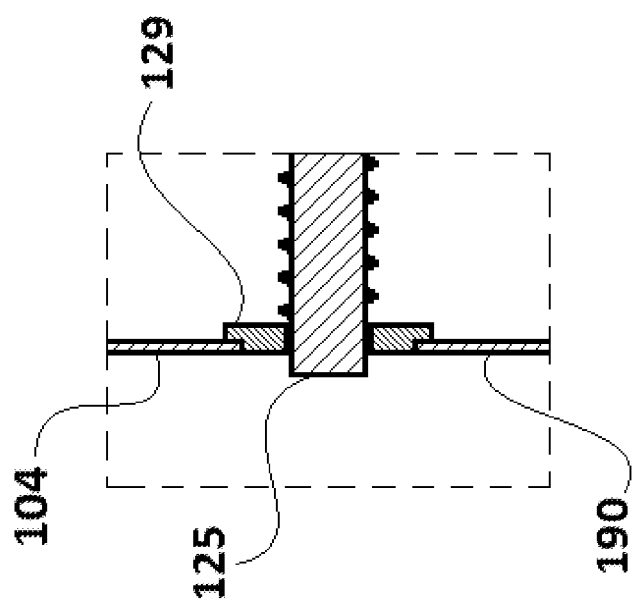

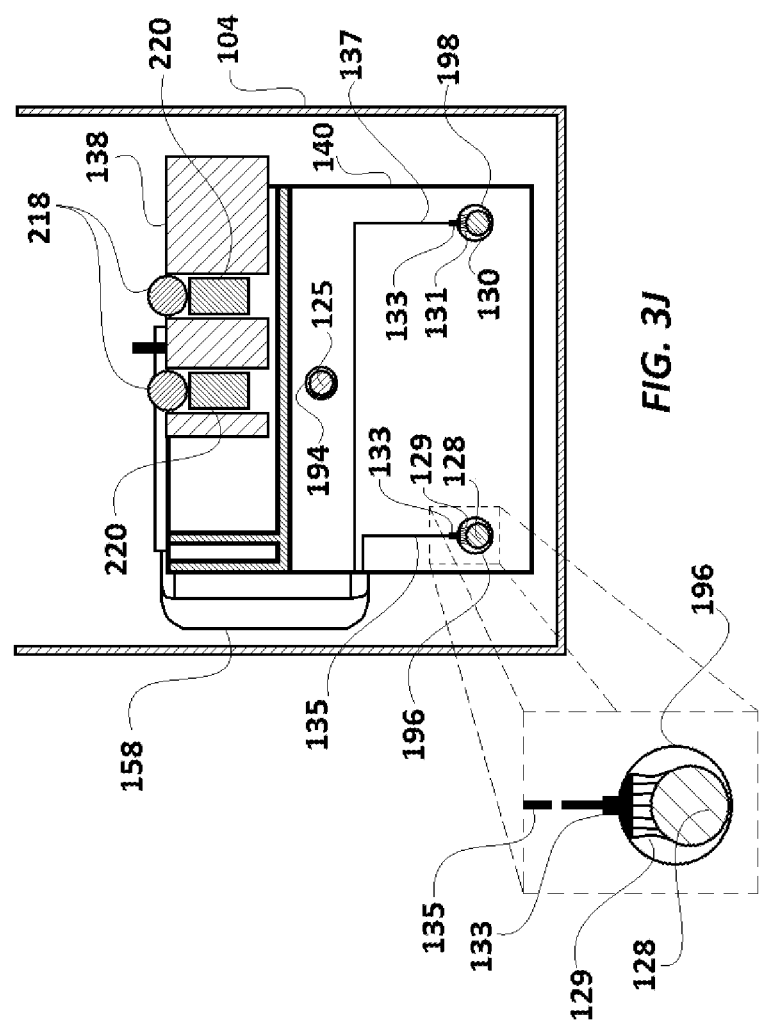

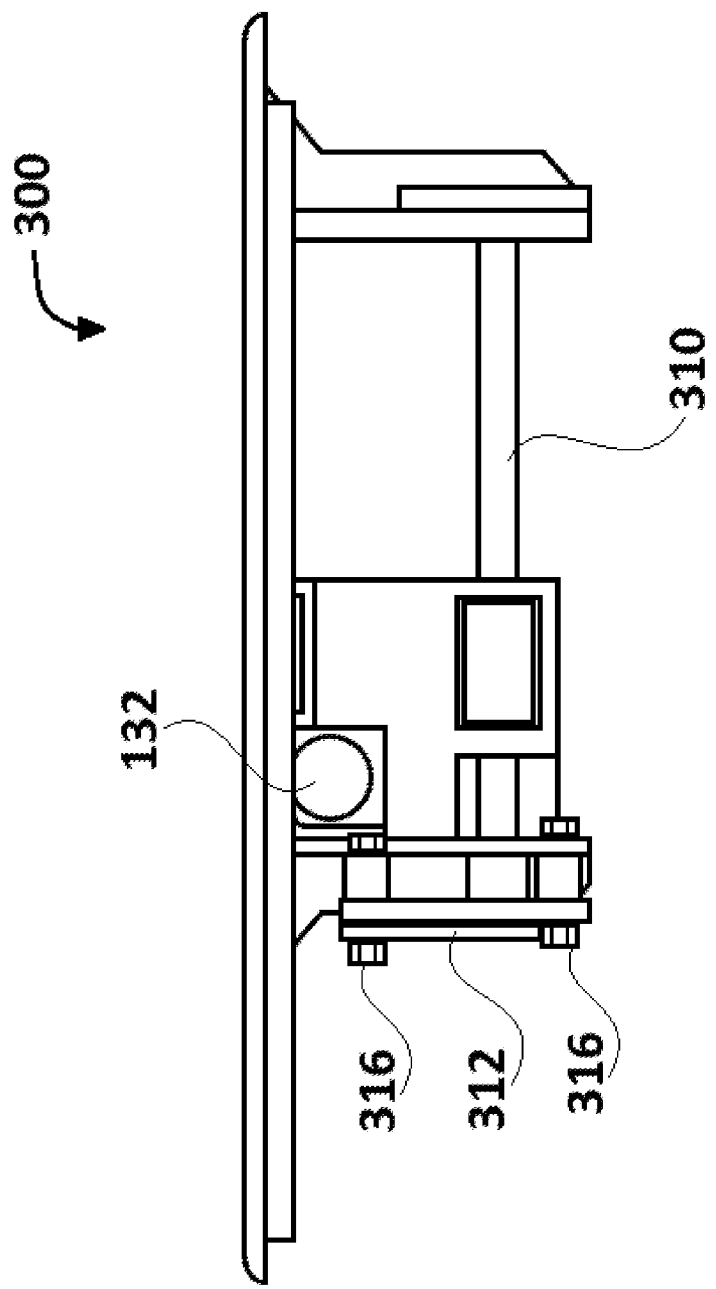

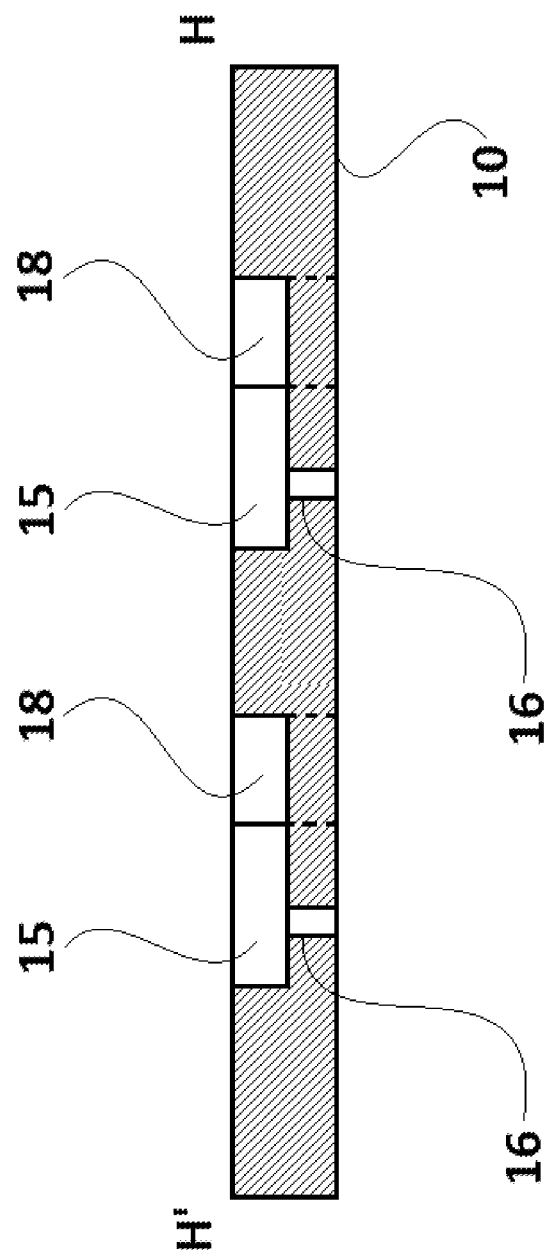

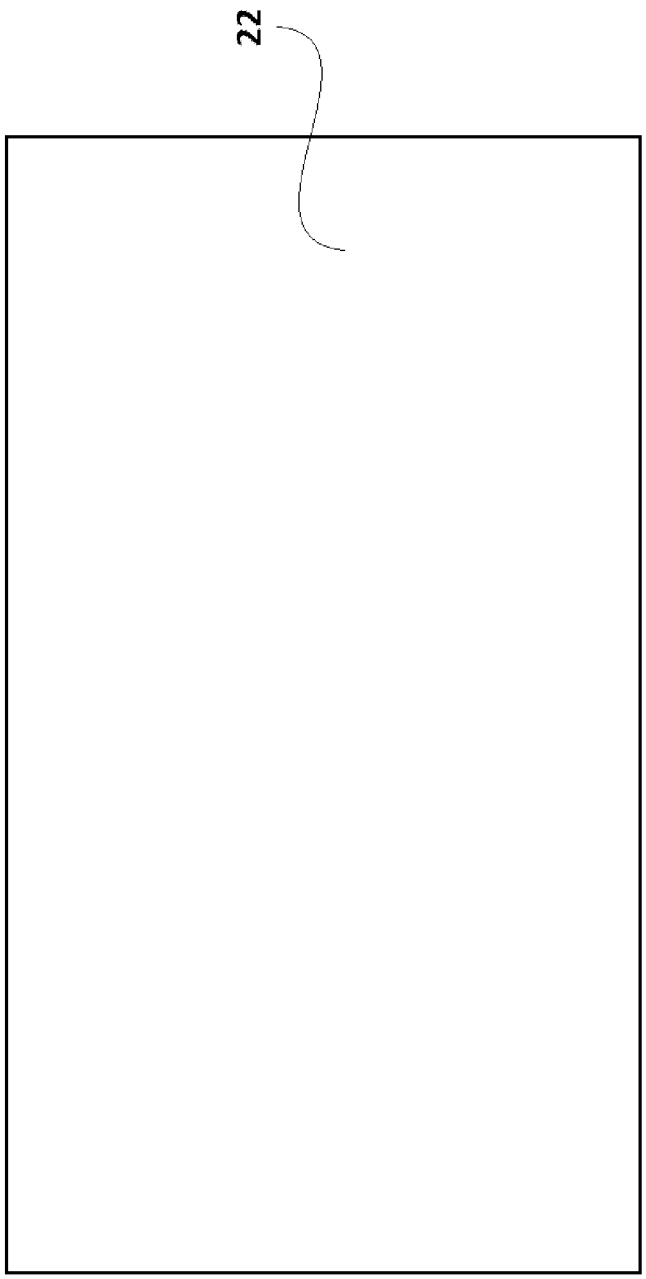

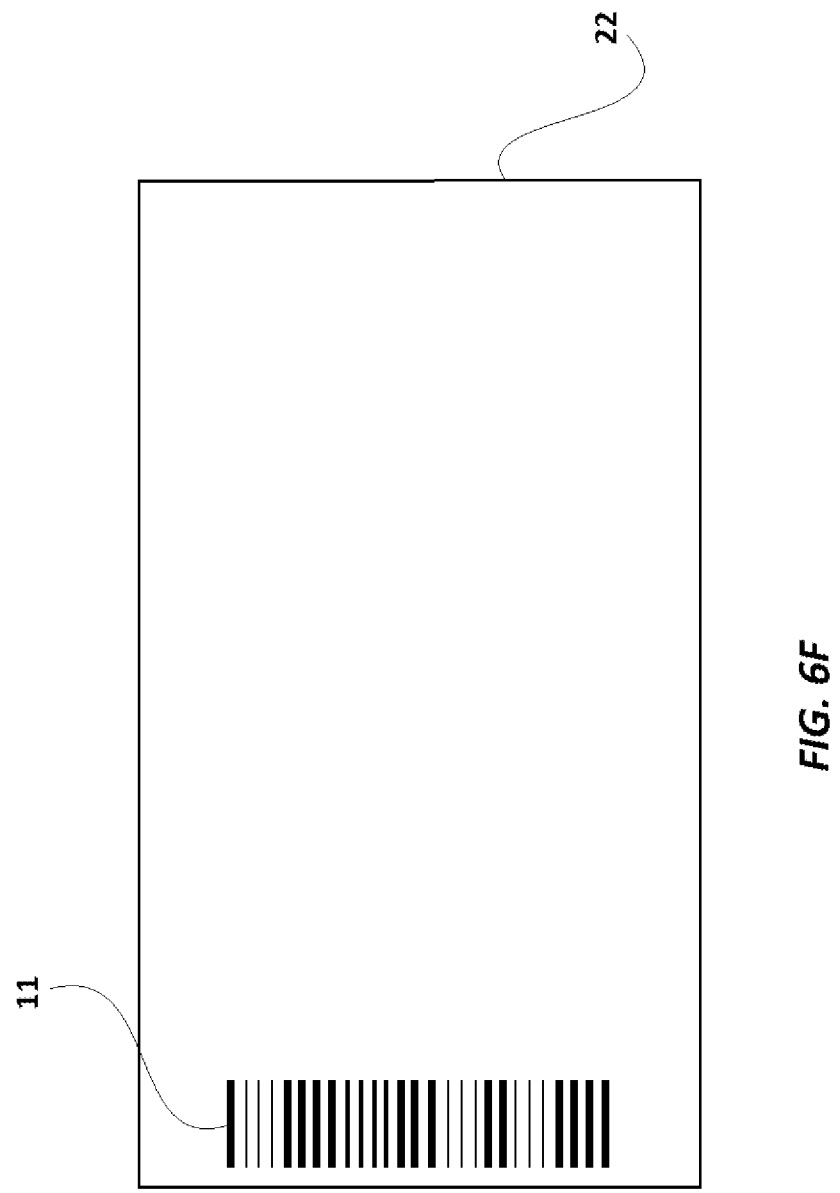

AUTOMATED DRIVING OF AN ASSAY

GOVERNMENTAL RIGHTS

This invention was made with governmental support under Grant Numbers 1R43DA041966-01; and 1R43DA043325-01, both awarded by the National Institute on Drug Abuse. The government has certain rights in the invention.

BACKGROUND

A reliable, robust assay system which can be deployed to a point of care is useful in a number of settings. For example, where there is an infectious disease outbreak in a remote area (e.g., the recent Ebola outbreaks), such an assay is of benefit for arresting the outbreak as quickly as possible (infected individuals can be quickly identified and then given medical care) and for keeping health care providers safer.

An assay driver system can be used to automate an assay. One type of assay driver induces movement of magnetic beads which contact sample (or control) and then carry it into contact with assay reagents. The movement has to be carefully timed, to ensure proper reaction times for different reagents. The results must also be readable for fast interpretation. One type of point of care assay system suitable for use with an assay driver herein is disclosed in US Publ'n No. 2016/0195523 (incorporated by reference). This application discloses a cartridge having wells containing various assay reagents. Magnetic beads also reside in the wells, and the magnetic beads are moved among the wells in order to carry sample into contact with different assay reagents in different wells.

An assay driver system can be used to automate the assay, by moving magnets (and carrying the magnetic beads) through the wells of the cartridge, and into contact with the assay reagents in various wells. The movement has to be carefully timed, to ensure proper reaction times for different reagents. The results must also be read and sent for interpretation, and to permit quick action. No current system automates these functions. Remote authentication of the cartridge (to provide the proper instructions to the driver) and automation of the individual assays which can be performed by the cartridge, coupled with reading and sending of assay results from the point of care is needed, to solve the problems associated with an infectious disease spreading rapidly among a population.

In addition to carefully timing the movement of magnetic beads to ensure proper reaction times between them and different reagents in currently known assay driver systems, during mixing of the beads with the reagents in wells of an assay cartridge, an appropriately sized and directed, and a properly moved magnetic field is required to ensure proper movement of the magnetic beads throughout each well, and proper mixing between magnetic beads and the reagents in each well.

Hence there is a need for an improved automated assay driver system which is more accurate, is more efficient, and facilitates faster interpretation of assay results.

SUMMARY

The invention is an apparatus and method for performing an assay where a sample or binding agent or antigen, carried by magnetic beads, is brought in contact with different assay reagents in different wells of an assay cartridge. The movement of magnetic beads among wells of the cartridge is driven and guided by controlled movement of magnets or a magnetic array, preferably including scanning magnets and corresponding orienting magnets. The magnets are preferably permanent magnets, such as rare earth magnets, though other means of generating magnetic force, including electromagnets, could be used. The movement of the magnets is controlled by an apparatus in accordance with a set of authenticated assay instructions.

In one embodiment the apparatus comprises a substantially transparent assay cartridge, a scanning platform for the assay cartridge, and an array of magnets installed in a magnet holder contained in a magnet carrier base. The magnet carrier base is moved by an externally threaded driving rod along two metallic rail rods that lie parallel to the driving rod. The array of magnets preferably further comprises a plurality of spherical scanning magnets which are oriented to align with the poles using a corresponding cylindrical orienting magnet for each scanning magnet. Each orienting magnet stands vertically, with one pole at the top, and aligned below its corresponding scanning magnet. The orienting magnets can be fixed, but the spherical magnets can preferably move in their holder enough such that the poles align the same way as the poles of the orienting magnets. The magnet carrier base resides under the scanning platform.

The assay cartridge preferably includes one or more series of wells, where each series of wells is arranged along a line parallel with the driving rod. In one embodiment, the cartridge has two series of wells, where one series has magnetic beads and control analyte in two of its wells, and assay reagents in others, and where the second series is identical to the first except that the sample is introduced in place of the control analyte. The magnet carrier base containing a magnet holder is positioned a specific distance below the scanning platform (having the assay cartridge placed on it) such that the magnetic beads in the assay cartridge experience a defined magnitude of magnetic field (provided by scanning magnets and orienting magnets). The magnet carrier base is movable with respect to the assay cartridge along a first axis (parallel to the driving rod), and the magnet holder is movable along a second axis, wherein the first axis intersects the second axis. Movement of the magnet carrier base along the first axis is powered by rotation of the externally threaded driving rod which extends through a mating threaded portion of the magnet carrier base; rotation of the externally threaded driving rod is driven by the shaft of a stepping motor which can move a specified increment and hold. Movement of the magnet holder along the second axis is powered by an electromagnet coil, such as a linear solenoid actuator, which moves the magnet holder on activation.

While moving along the first axis, the magnet carrier base preferably slides on two rail rods which extend through the magnet carrier base. The two rail rods prevent skewing of the magnet carrier base while moving along the first axis. Further, the two rail rods may also be in electrical contact with the electromagnet coil which, when actuated by applying an electrical potential difference across the rods, moves the magnet holder along the second axis. A compressible spring provided with the magnet holder causes the magnet holder to return back along the second axis when the coil is de-actuated or when the potential applied to the coil is substantially reduced from the actuating potential.

To automate the movement of the magnet carrier base and magnet holder (and the array of magnets) within a predefined two-dimensional space (in the directions of the first and the second axes), the device is further equipped with a microcomputer, which controls the operations of the stepping motor, and varies the levels of electrical potential difference applied to the coil. The microcomputer is powered by a DC power source included in the device.

To conduct an assay, a loaded assay cartridge (preferably having a sample, control analyte, magnetic beads and reagents loaded in wells) is placed on the scanning platform. Based on a QR or barcode identifier, the cartridge identity is authenticated and a set of assay instructions are sent to the device. The microprocessor drives and guides movement of the magnet carrier base and magnet holder (and the array of magnets) by executing the instructions. The magnetic beads follow movement of the scanning platform, and travel from one well to another to interact with different reagents in performance of the assay.

Embodiments of the invention are discussed in greater detail with reference to the accompanying figures in the detailed description which follows.

BRIEF DESCRIPTION OF DRAWINGS

FIG. 3B is a perspective view of the motor shaft.

FIG. 3E and FIG. 3F, respectively show an exploded sectional view and a sectional view as in use, of the two-piece pivot pin assembly holding together the scanning box and driving box (as shown in FIG. 1C).

FIG. 3I is a cross-sectional view of the portion of the device shown in FIGS. 2A and 2B as indicated by the lines D-D'.

FIG. 3J is a cross-sectional of the device shown in FIGS. 2A and 2B, taken along the lines B-B' in FIG. 2B.

FIG. 3K is an up close view of the portion indicated in FIG. 3J by dotted lines.

FIG. 3N is a side view of the device in FIG. 3M.

FIG. 5E illustrates a cross-sectional view of assay cartridge of FIG. 5B taken along lines H-H'.

FIG. 6D is a plan view of the lower side of the assay cartridge with the cover in place.

FIG. 6F is a plan view of the inner side of the cover layer.

Figure 1A:
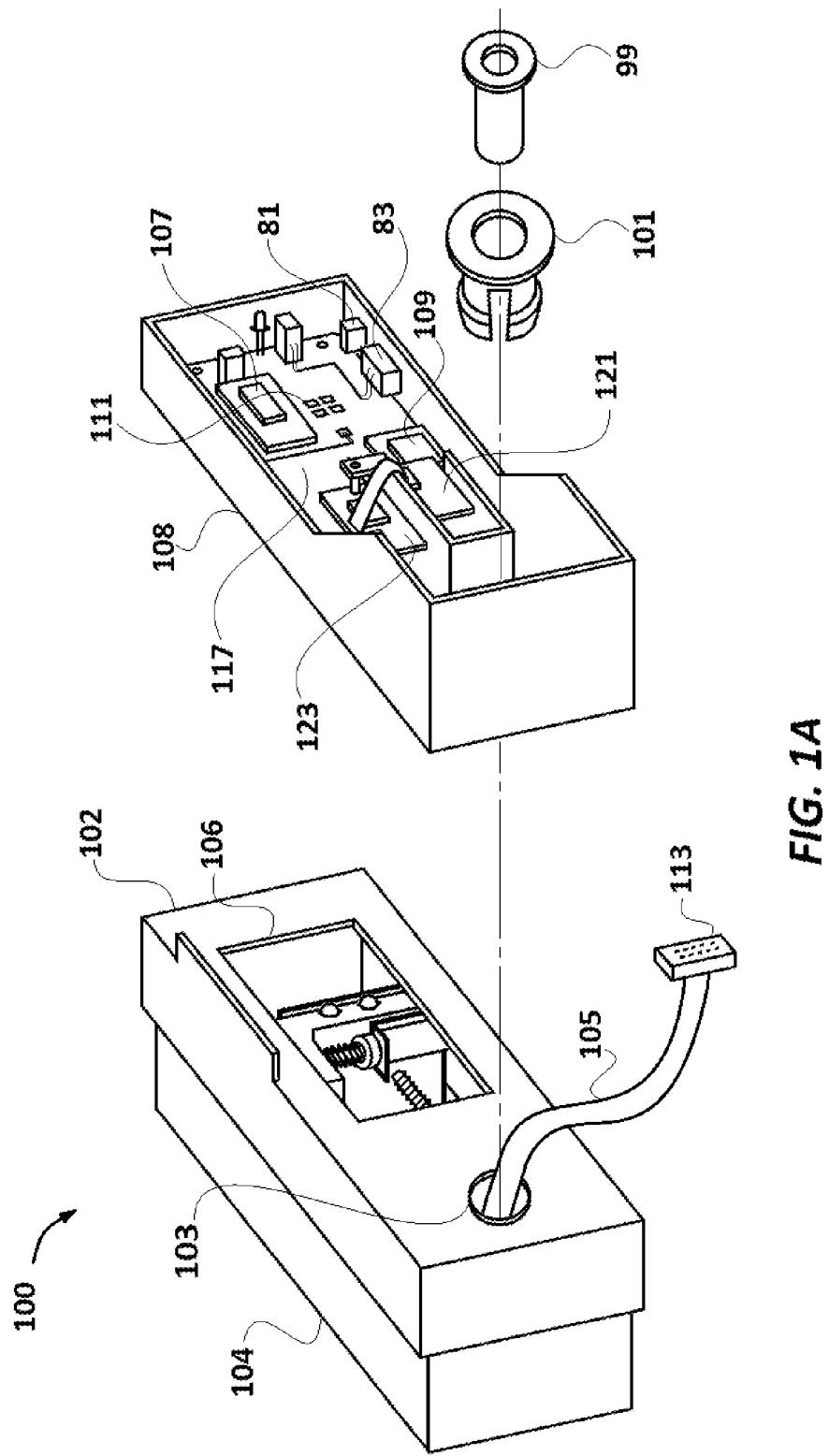
FIG. 1A illustrates an exploded view of the assay driver showing the scanning box and the driving box separated.

It should be understood that the drawings and the associated descriptions below are intended only to illustrate one or more embodiments of the present invention, and not to limit its scope. The drawings are not necessarily to scale.

DETAILED DESCRIPTION

The term "magnetic beads" refers to bead-shaped objects of any size (including microbeads) and composition which can be attracted or repulsed by a magnetic force, including objects containing paramagnetic materials or magnetizable materials, such as conductors, and including conductive metals.

Reference will now be made in detail to a first embodiment of an assay device of the invention with reference to the accompanying figures. As illustrated in FIGS. 1A to 2B, assay driver 100 comprises a driving box cover 102 and a driving box 104. Cover 102 serves as a cover for the driving box 104 and includes a scanning platform 106 where a loaded assay cartridge 10 (covered with covered with layer 20 and cover 22 to form assembly 78, as in FIG. 6A) is placed for scanning (either or both, before and following the assay, see below). The term 'loaded assay cartridge' is meant to designate an assay cartridge which is filled or loaded with some or all of a sample ready to be analyzed, a control, assay reagents, and magnetic beads.

Driving box cover 102 includes hole 103 where cable 105 with microcomputer connector end 113 extends through. Pivot pin 101 and lock member 99 are shown exploded in FIG. 3E and as used when functioning, in FIG. 3F. Pivot pin 101 mates into hole 103, and can be locked with lock member 99 which forces the lower flanges on pivot pin 101 outwards, as shown in FIG. 3F. Pivot pin 101 forms a pivot point for scanning box 108 relative to driver 100. FIG. 1C shows a pivoted position of the scanning box 108 relative to driver 100.

Scanning box 108 includes a main circuit board 117 which has a microcomputer 107, a mating connector 119 (shown in outline) for connector end 113, a bluetooth unit 109 (GSM-HSPA), a QR scanner 121, and QR circuit board 123 allowing reading the codes to identify the loaded assay cartridge assembly 10, when it is placed on scanning platform 106. Scanning box 108 also includes battery pack 9, DC input port 81 (which can be connected with a power source) and on-off switch 83.

Figure 1B:
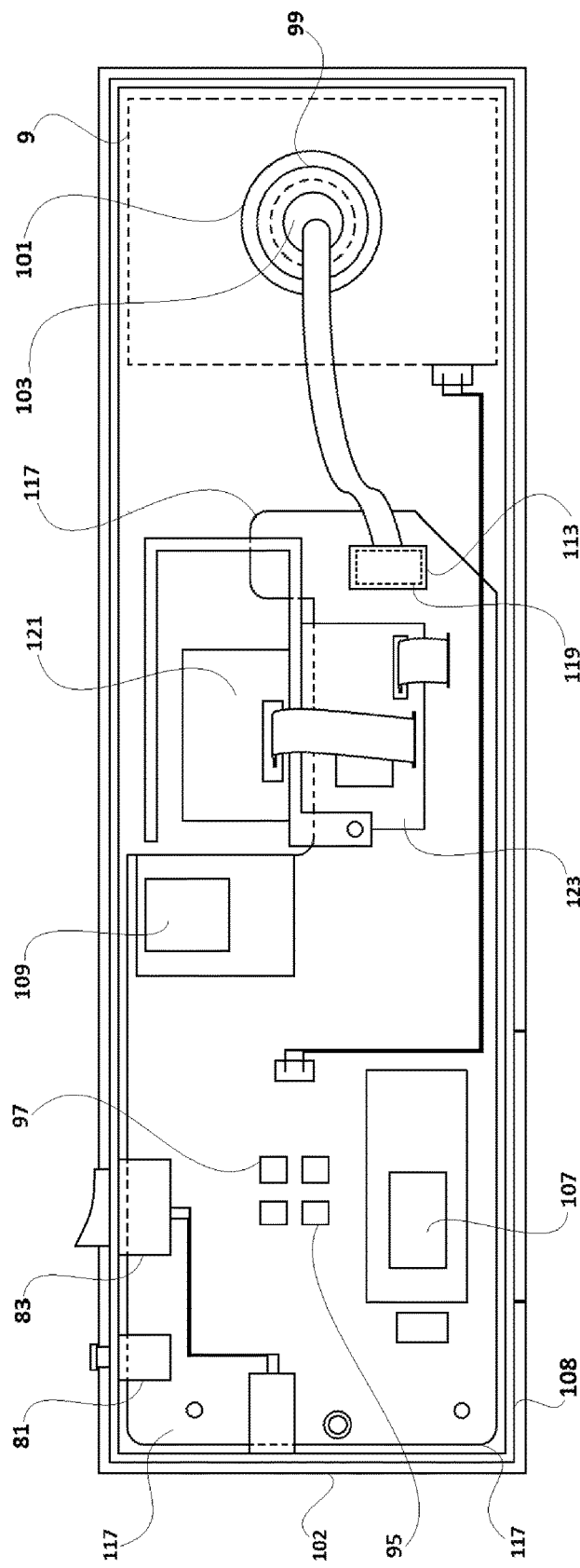
FIG. 1B is a plan view of the scanning box (driving box not shown).
Figure 1C:
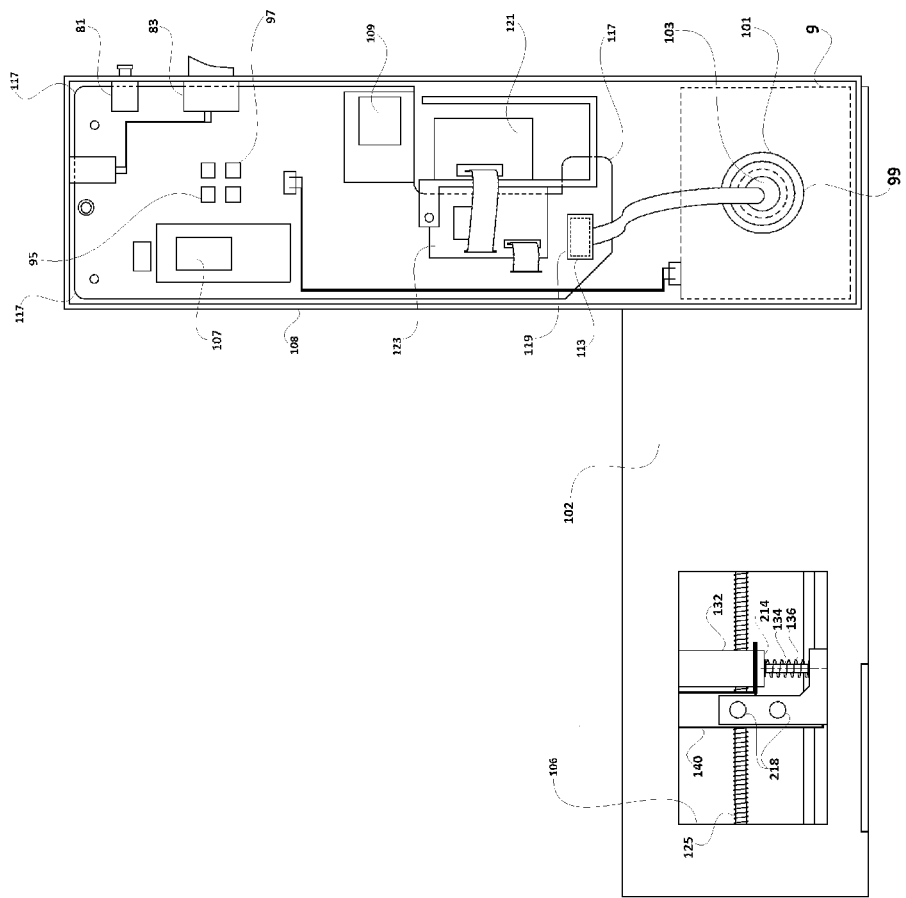
FIG. 1C is a plan view showing the scanning box joined to the driving box and rotated to an orthogonal position.
Figure 3A:
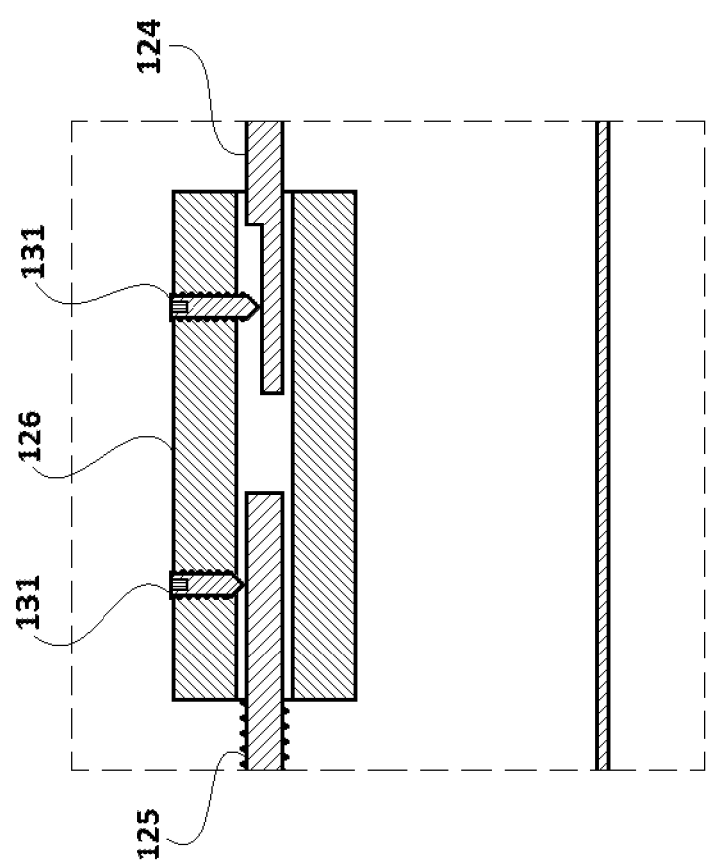
FIG. 3A illustrates a cross-sectional view taken along the lines C-C' of FIGS. 2A and 2B.
Figure 3D:
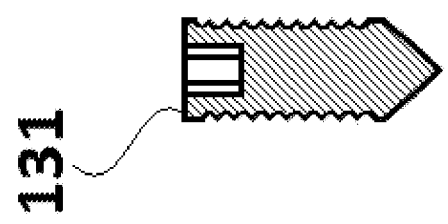
FIG. 3C and FIG. 3D show a perspective view and a sectional view (along the lines D-D' of FIG. 3C), respectively, of the screws holding the motor shaft and linking it to a driving screw, as shown in FIG. 3A.
Figure 3C:
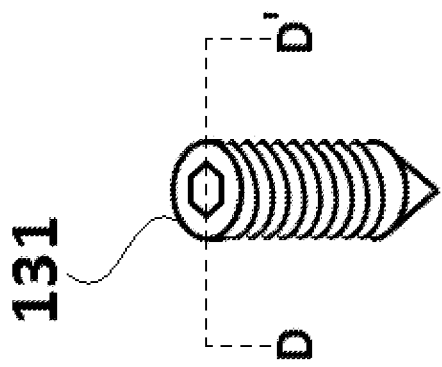
Figure 3H:
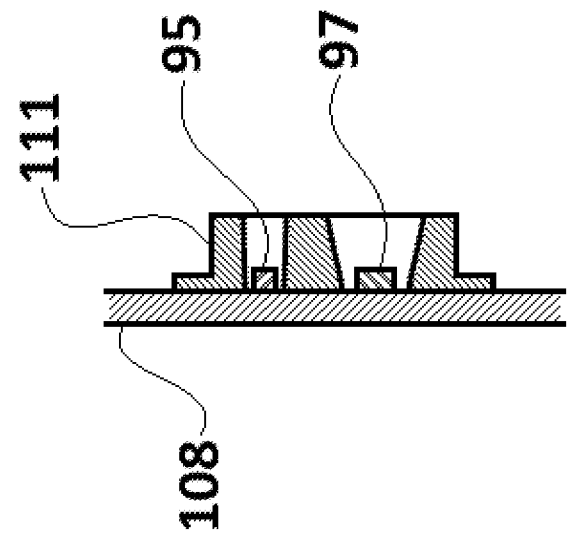
FIG. 3G and FIG. 3H, respectively, show a plan view of the portion of the scanning platform (as shown in FIG. 1B) with the LEDs and the sensor, and a cross-sectional view of it along the lines G-G'.
Figure 3G:
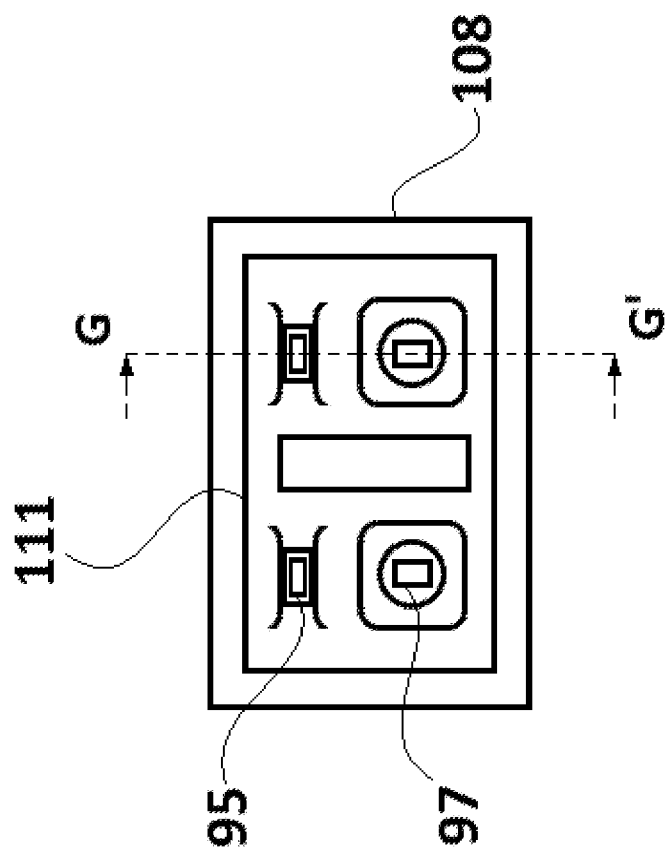
Figure 5A:
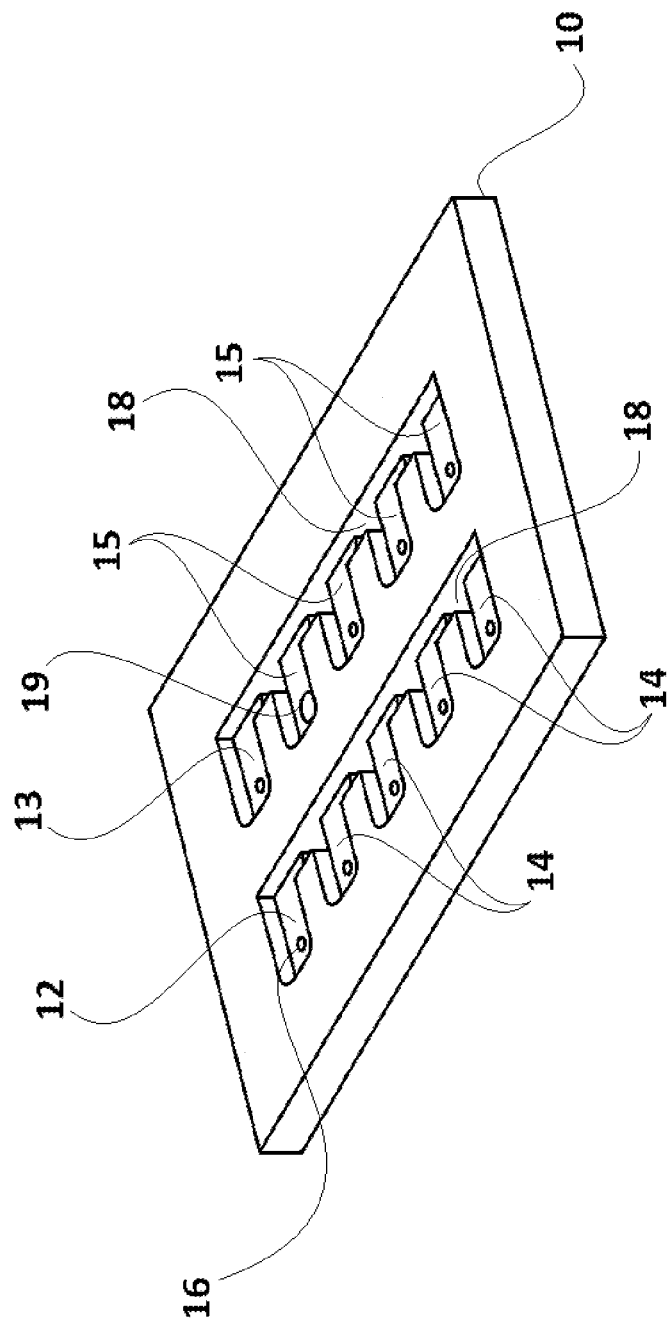
FIG. 5A is a perspective view of one embodiment of an assay cartridge.
Figure 5B:
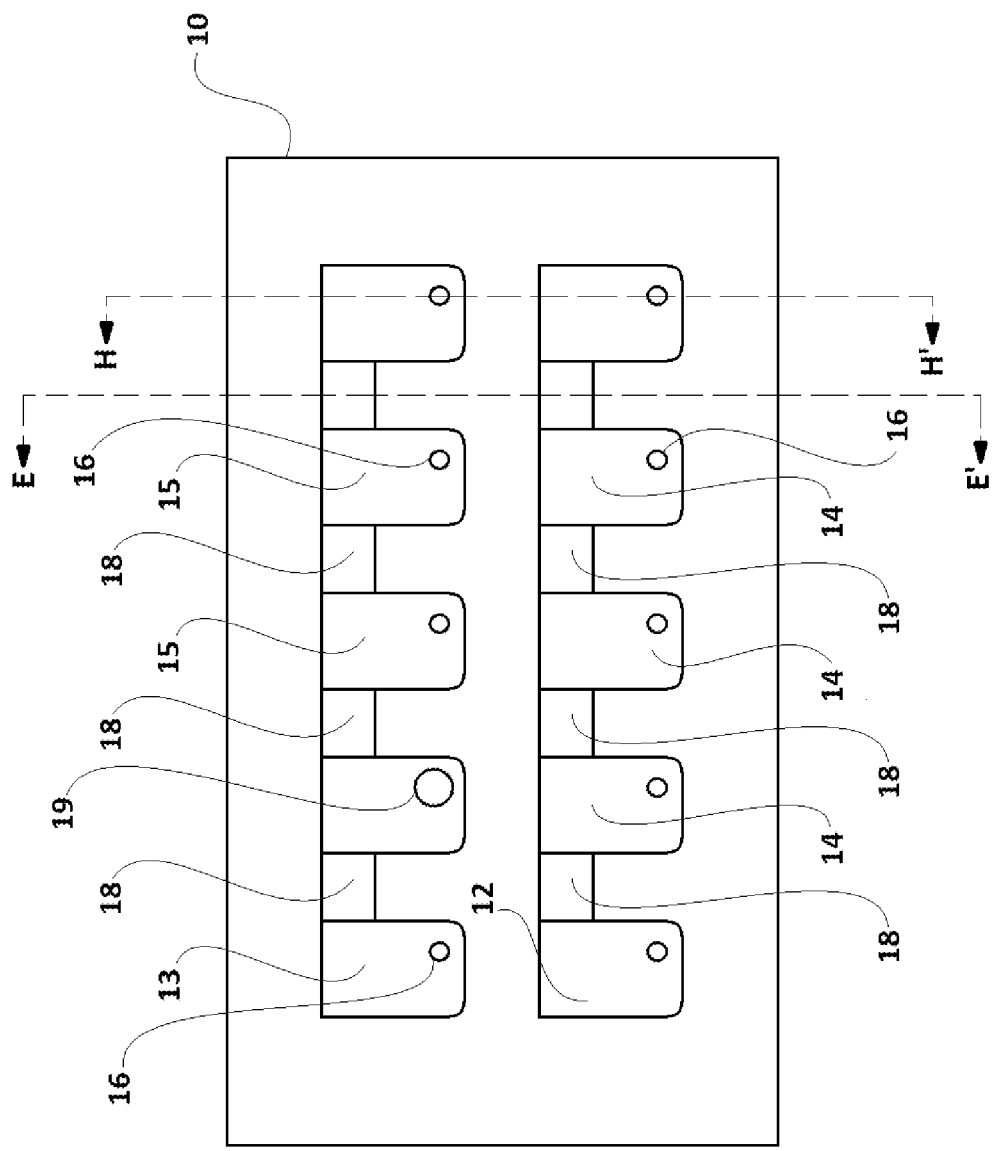
FIG. 5B is a plan view of the assay cartridge base of FIG. 5A.
Figure 5C:
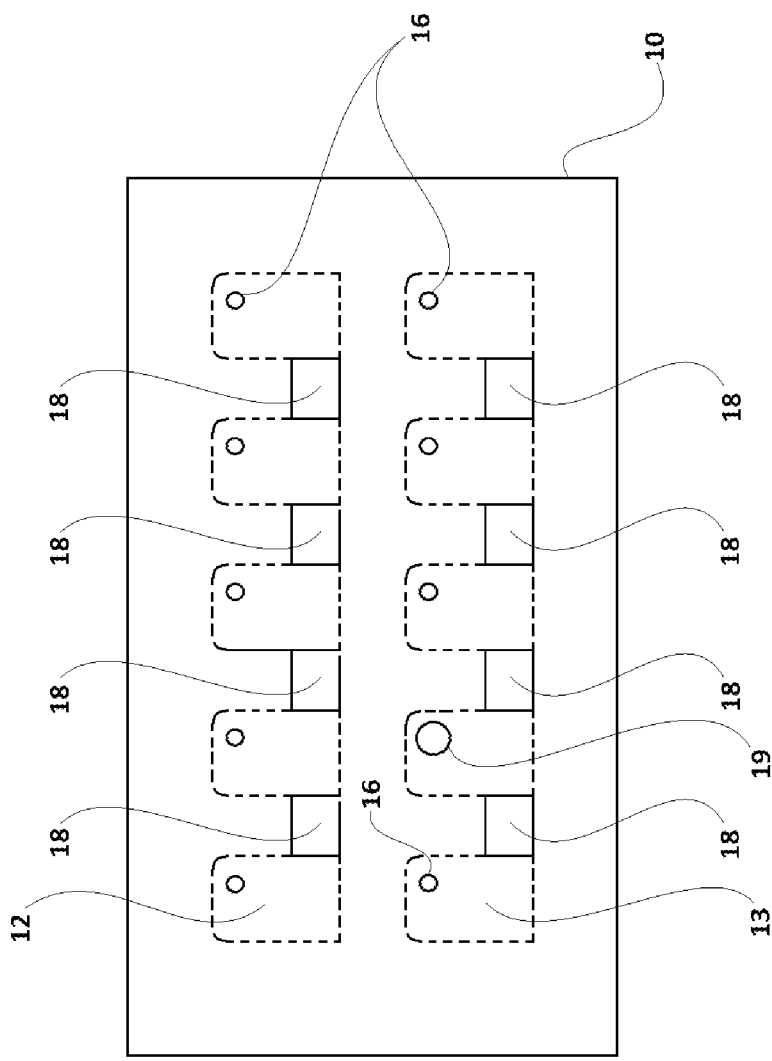
FIG. 5C is a plan view of the opposite side of the assay cartridge of FIG. 5B.
Figure 5D:
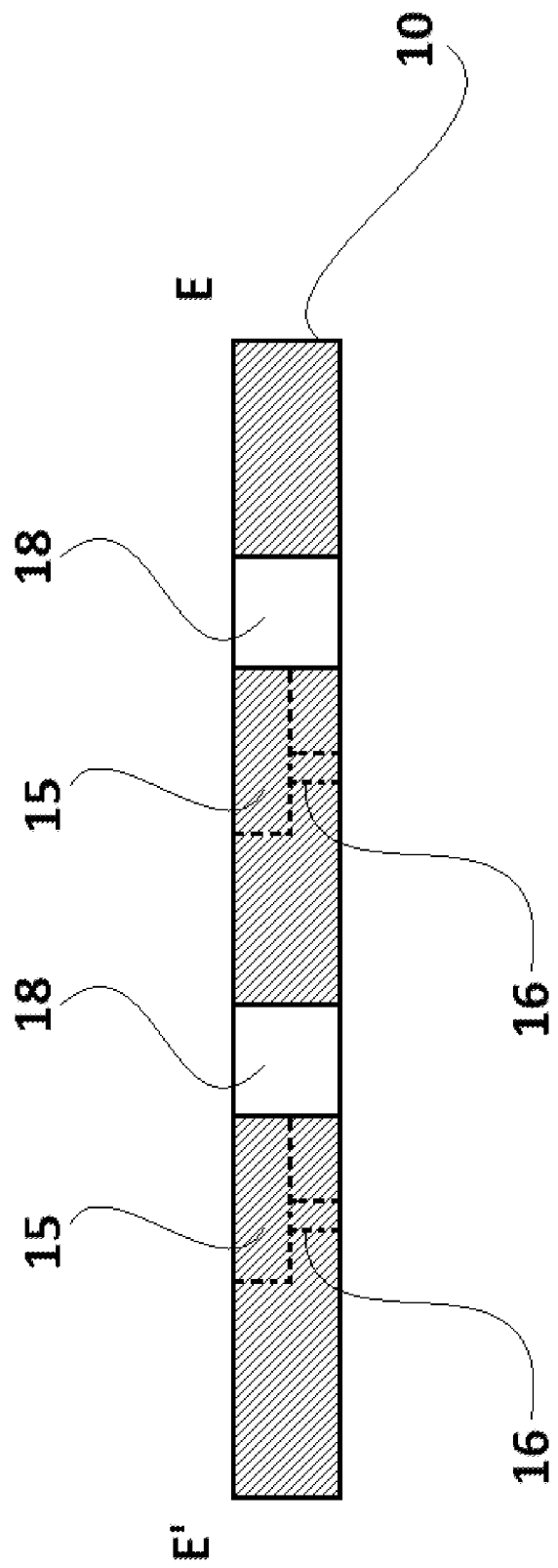
FIG. 5D is a cross-sectional view of assay cartridge of FIG. 5B taken along lines E-E'.
Figure 6A:
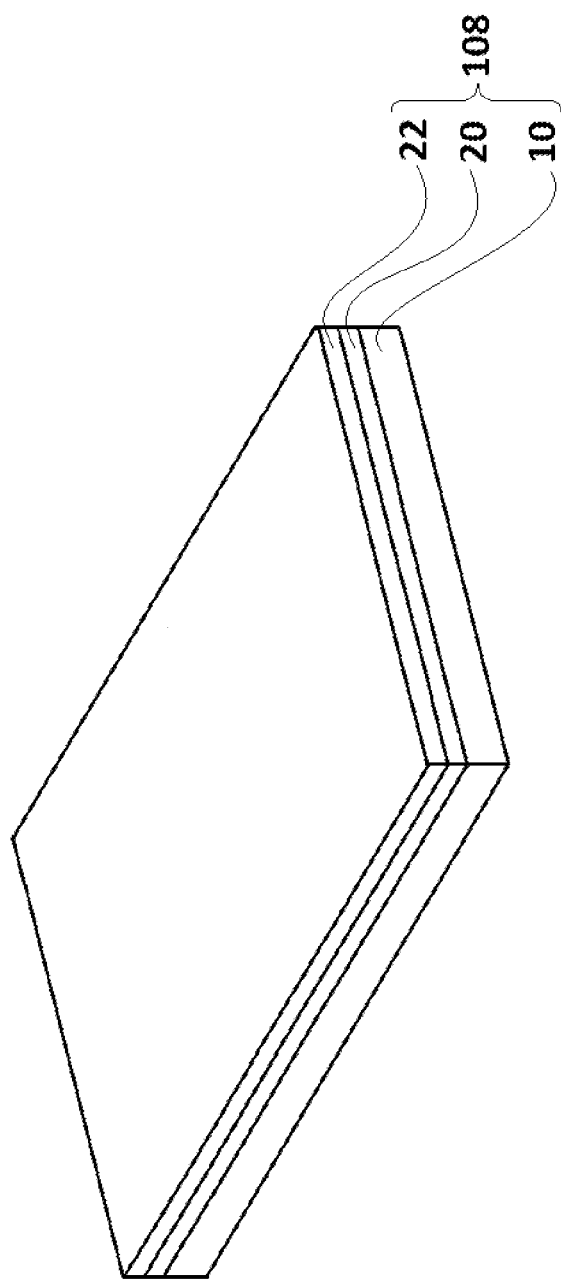
FIG. 6A is a perspective view of an assay cartridge assembly with a first layer and a protective cover layer in place.
Figure 6B:
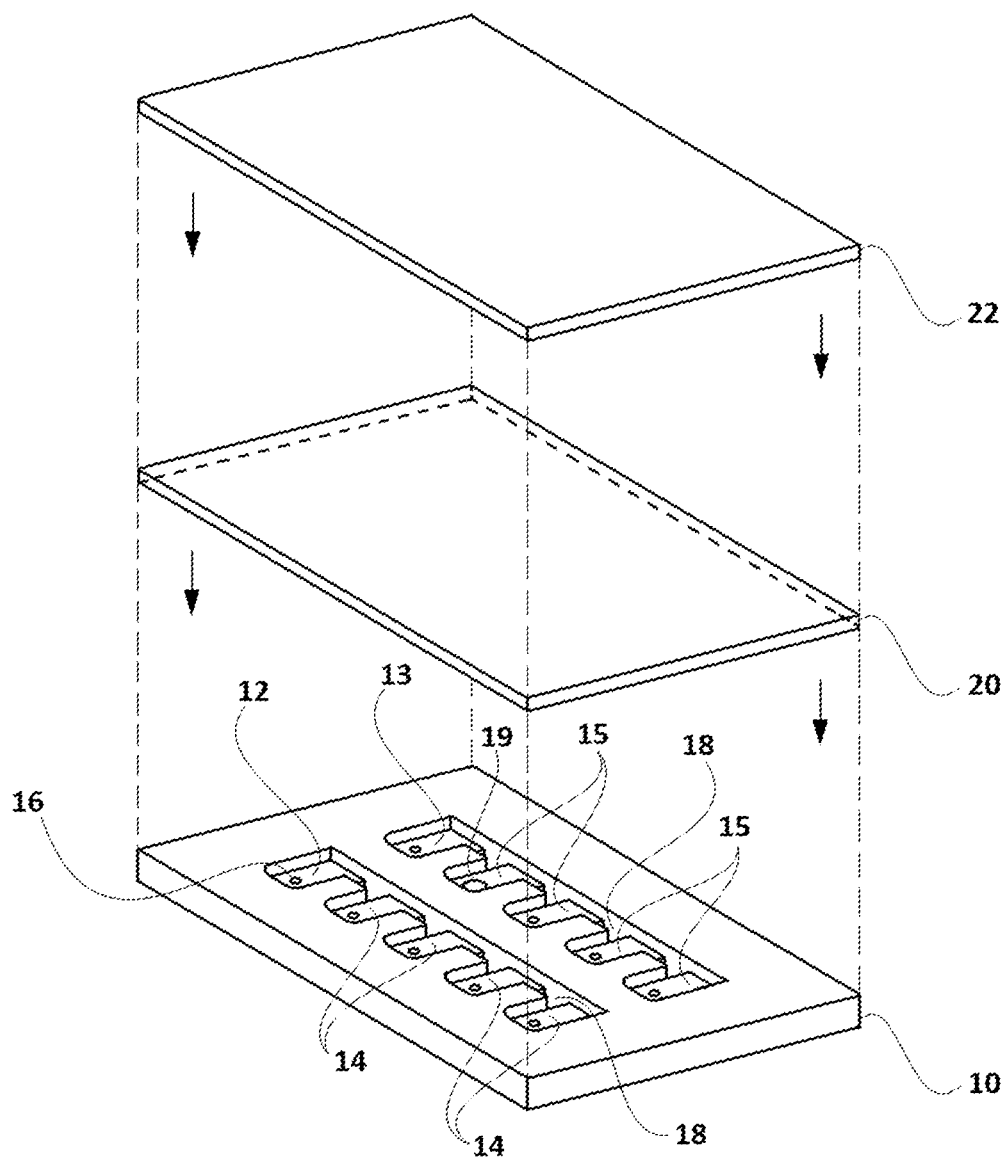
FIG. 6B is an exploded, elevational view of a first layer and a cover layer for the assay cartridge assembly shown in FIG. 6A.
Figure 6C:
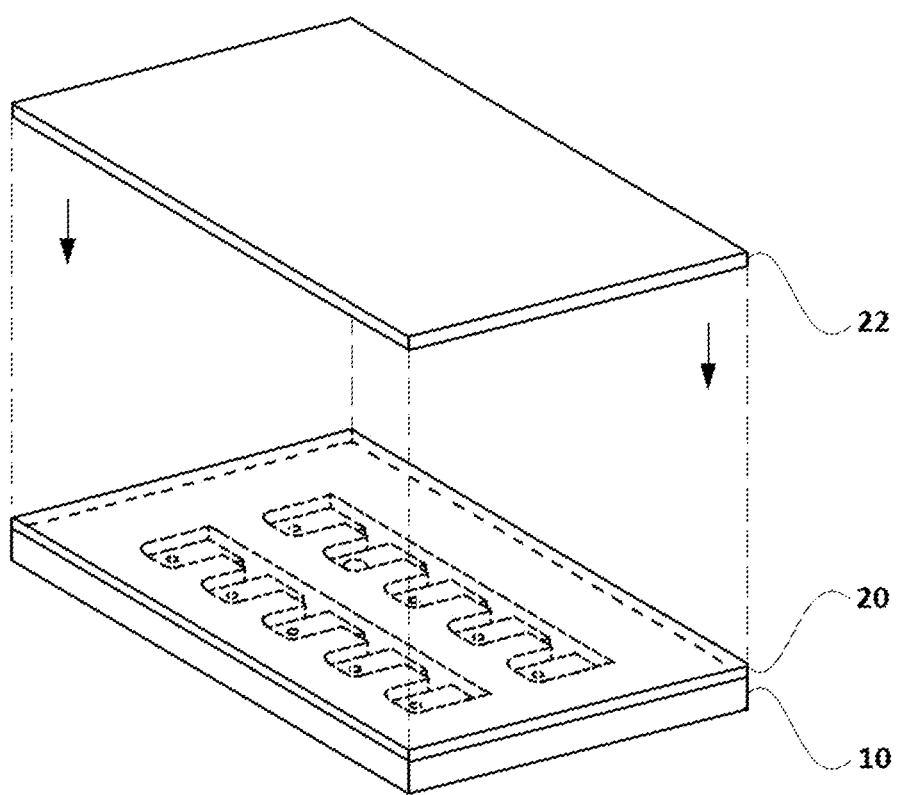
FIG. 6C is a perspective view of the assay cartridge assembly shown in FIG. 6A with the first layer in place and the cover separated.
Figure 6E:
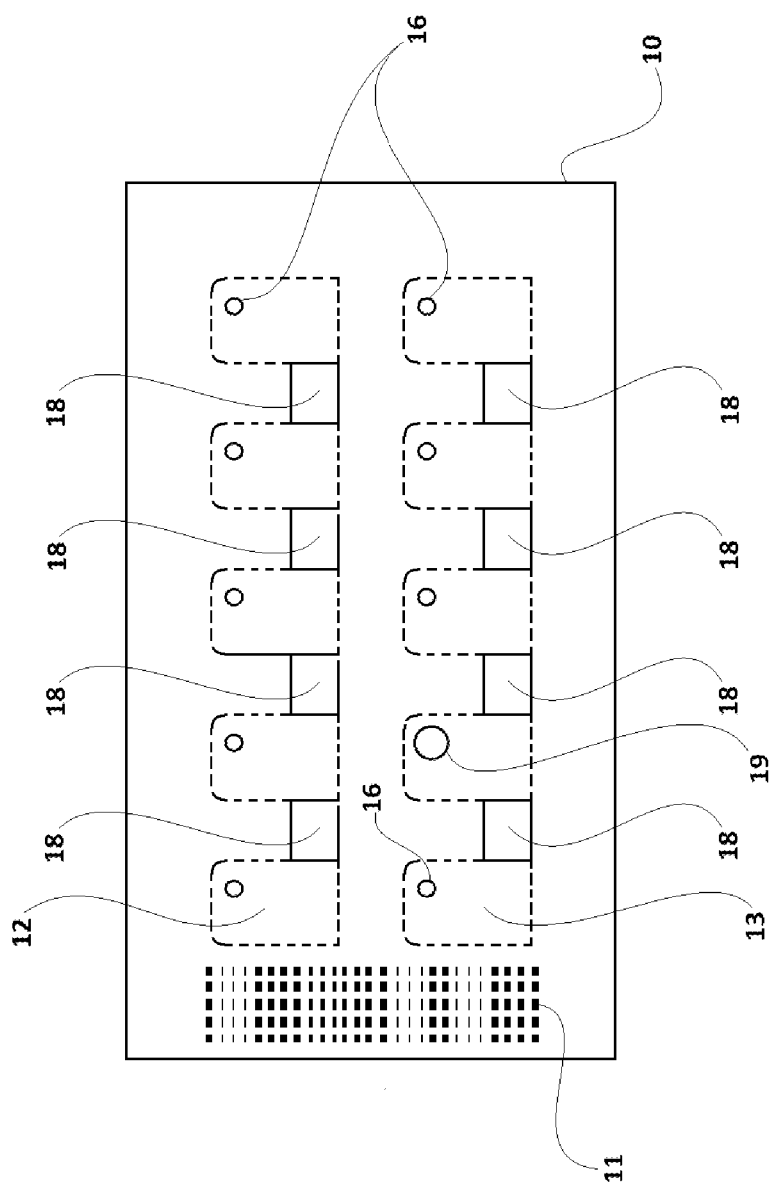
FIG. 6E is a plan view of the side of the assay cartridge shown in FIG. 6D with the first layer and the cover in place.

As seen in FIGS. 1B, 3G, and 3H, main circuit board 117 includes LEDs 95 and sensors 97, which together illuminate and capture images of loaded assay cartridge assembly 78 from the side shown in FIGS. 5C and 6E, because the view of the other side (shown in FIGS. 5A and 5B) is obstructed by cover 22. Light guide 111 is aligned with LEDs 95 and sensors 97 to limit their field of view.

Figure 2A:
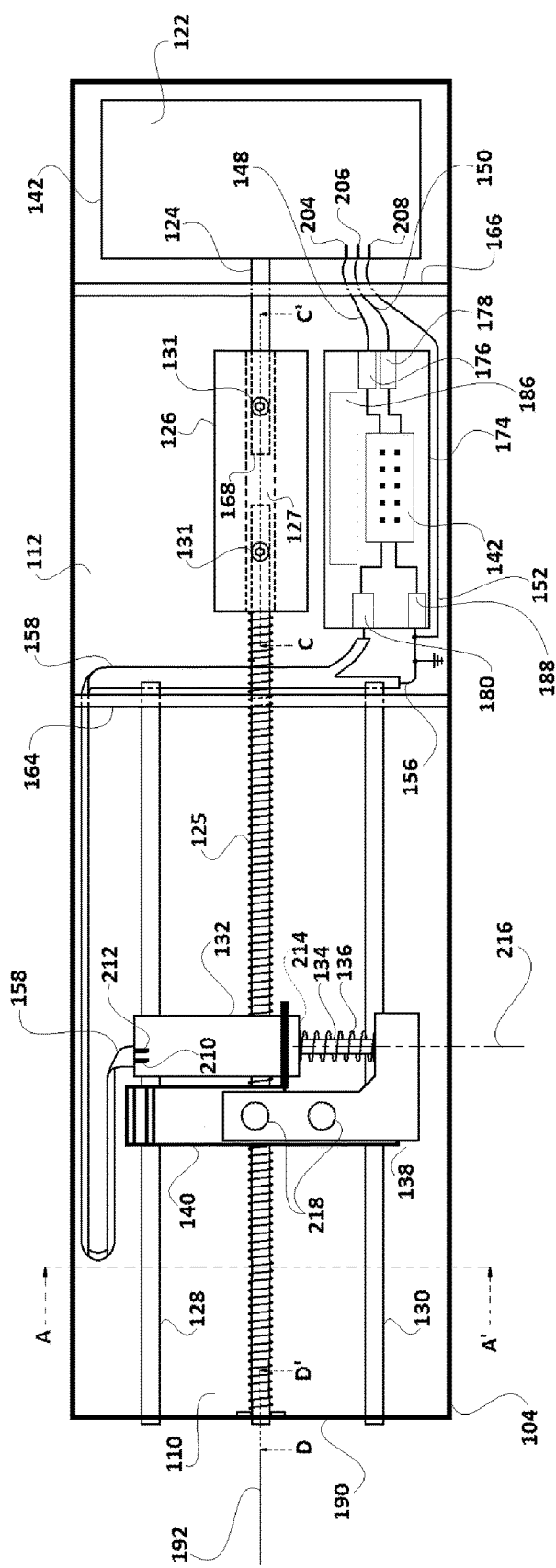
FIG. 2A is a plan view showing the insides of the driving box of FIG. 1C with the scanning box removed.
Figure 2B:
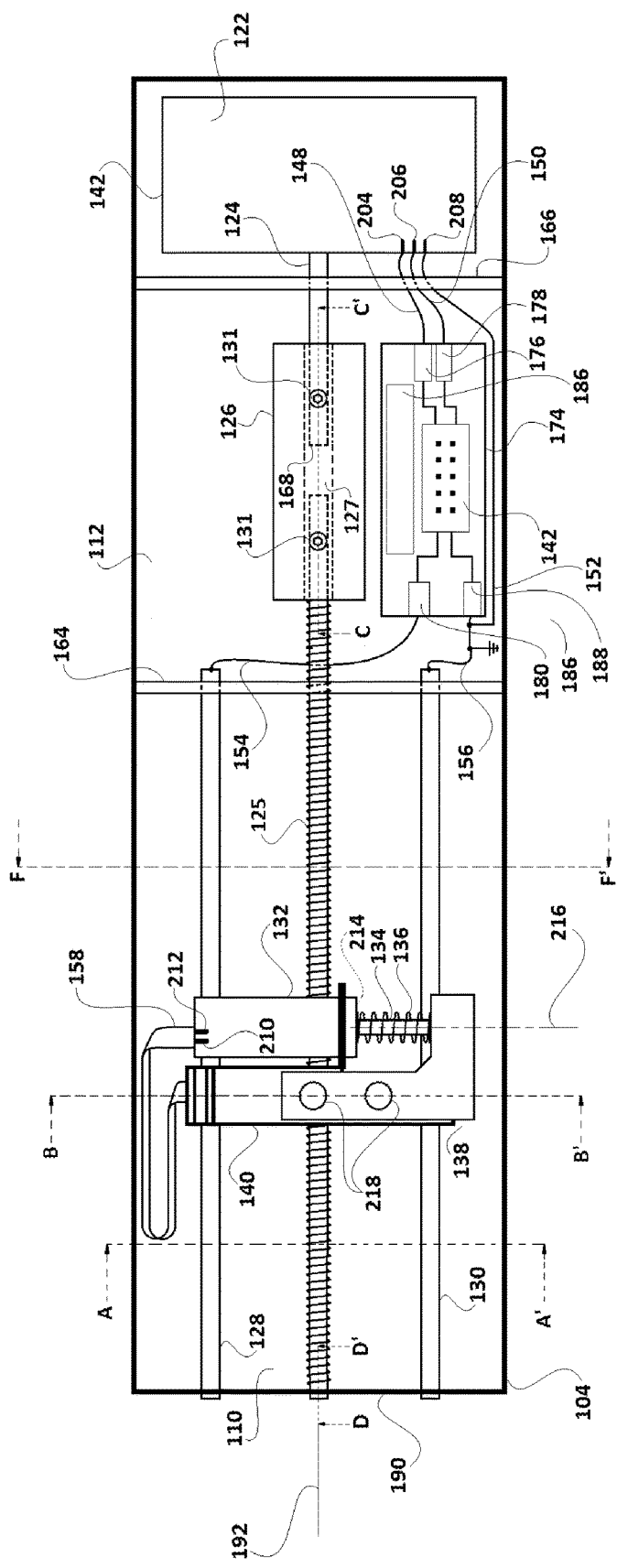
FIG. 2B is a plan view of a related embodiment to that in FIG. 2A, wherein the rods provide electrical connection from the microcomputer to the solenoid.

Referring to the two different embodiments shown in FIGS. 2A and 2B, driving box 104 includes a first compartment 110, a second compartment 112, a third compartment 141, a stepping motor 122, a metallic driving shaft 124 of the motor 122, a partially threaded metallic driving rod 125, a coupling cylinder 126, a first rail rod 128, a second rail rod 130, a solenoid 132, a solenoid shaft 134, a compressible spring 136, a magnet holder 138, a magnet carrier base 140, a circuit board 142, insulated electric conductor wires 144, 146, 148, 150, 152, 154, 156, and ribbon electric connector 158 (located differently in the embodiments in FIGS. 2A and 2B). The first compartment 110 and the second compartment 112 are separated by a common wall 164, and the second compartment 112 and the third compartment 141 are separated by a common wall 166.

While the solenoid 132, the solenoid shaft 134, the compressible spring 136, the magnet holder 138, and the magnet carrier base 140 lie in first compartment 110, the coupling cylinder 126, and connector 142, lie in the second compartment 112. The DC stepping motor 122 lies in the third compartment 141.

FIG. 2A illustrates an embodiment where ribbon 158 connects solenoid 132 to circuit board 142. FIG. 2B illustrates an embodiment where solenoid 132 connects to circuit board 142 through first and second rail rods 128 and 130 and then through ribbon 158. Rail rods 128 and 130 are made of electrically conductive material (preferably a metal) and are laid bare (i.e. without an insulation cover) within the driving box 104. In this embodiment, ribbon 158 could be insulated wires instead of a ribbon connector. One could also connect ribbon 158 (FIG. 2A) directly with circuit board 142, instead of to rail rods 128 and 130 or through wires 152, 154 or 156. Other means of electrically connecting solenoid 132 with a power source are also within the scope of the invention. Thus, instead of being powered as in FIGS. 2A and 2B, the input 210 of solenoid 132 can be connected to the first and second rail rods 128 and 130 (FIGS. 2A and 2B) through two separate brushes 129 and 131, which make sliding contact with rail rods 128 and 130, as shown in FIGS. 3J and 3K, and those brushes connect through ribbon 158 to solenoid 132 (not shown in FIG. 3J) In the embodiments shown in FIGS. 3J and 3K, brushes 129, 131 are held by structures 133 and connected by wires 135 and 137 to ribbon 158, which is connected with solenoid 132.

In another embodiment, instead of ribbon 158 or brushes as in FIGS. 3J and 3K, one could attach conductive tape to the inside wall of a driving box 104, and have brushes extending from magnet carrier base 140 which make contact to form an electrical connection between solenoid 132 and the conductive tape, which is in electrical contact with outputs 180 and 188. In another embodiment shown in FIG. 3L, longitudinal strips 139 and 141 are selectively electrified and connect to solenoid 132 through brushes 143 and 145, respectively, which connect with ribbon 158 (which is connected to solenoid 132).

Referring to FIGS. 2A and 2B, first and second rail rods 128 and 130, as well as threaded driving rod 125, extend through the first compartment 110 into the second compartment 112. The driving shaft 124 extends through the third compartment 141 into second compartment 112.

Coupling cylinder 126 couples the metallic driving shaft 124 and the threaded driving rod 125 and keeps them aligned along a common axis 192. A longitudinal bore 127 extends through the coupling cylinder 126. An unthreaded end of the threaded driving rod 125 and of the metallic driving shaft 124 extend into the bore 127 form its opposite ends. FIG. 3A shows a sectional view of the portions of metallic driving shaft 124 and the threaded driving rod 125 extending into coupling cylinder 126, and FIG. 3B shows that section of driving shaft 124. Screws 131 connect as illustrated to hold driving shaft 124 and the driving rod 125 in place in coupling cylinder 126.

In alternative embodiments, other means to couple the threaded driving shaft 124 with the coupling cylinder 126 may be used. For example, a fully threaded driving shaft 124 and rod 125 could be screwed into either end of the coupling cylinder 126, or welded into the coupling cylinder 126, or mechanically joined with gears and sprockets.

Connector 142 from main circuit board 117 provides connection to the stepping motor 122 through outputs 176, 178, and connection to solenoid 132 through outputs 180 and 188. Wires 152 and 156 are preferably grounded as shown. The main circuit board 117 obtains electrical power from input 81.

Optional external inputs to microcomputer 107 from external memory devices (such as flash memories) are connectable to the microcomputer 107 through ports (such as USB ports, not illustrated), and can be included. Further, wireless inputs (for example, to receive instructions from a remote server) can also be provided for microcomputer 107 through the Bluetooth unit 109. When instructed wirelessly through unit 109, unit 109 can wirelessly transmit data generated by assay driver 100 (such as assay data or scanned images of the assay cartridge 10) to intended destinations, such as to an associated server. Further, unit 109 also facilitates wireless communication with associated external devices (such as servers and wireless handheld devices). See FIG. 7.

As a result of the coupling provided at the coupling cylinder 126, when driving shaft 124 is rotated by stepping motor 122, coupling cylinder 126 and threaded driving rod 125 also rotate in the same direction. Longitudinal movement of threaded driving rod 125 along its longitudinal axis 192 is prevented by having the end of driving rod 125 extend through an annular bearing 129 residing in wall 190, such that threaded driving rod 125 is freely rotatable around the longitudinal axis 192. See FIG. 3I.

The stepping motor 122, shaft 124, threaded driving rod 125 and coupling cylinder 126 may be installed within the driving box 104 such that the axis 192 divides the driving box 104 into substantially symmetrical halves. The ends of the first rail rod 128 and the second rail rod 130 are supported by wall 190. Further, first rail rod 128 and second rail rod 130 lie parallel to axis 192. Driving shaft 124 and threaded driving rod 125 pass through apertures in walls 166 and 164 respectively, which are sized and designed to not hinder rotation of driving shaft 124 or threaded driving rod 125.

In the first compartment 110, first rail rod 128, second rail rod 130 and threaded driving rod 125 pass through magnet carrier base 140. Functionally, when the threaded driving rod 125 is rotated in a first direction, induced by rotation of driving shaft 124 by stepping motor 122 in the first direction, the magnet carrier base 140 (which is screwed with the threaded driving rod 125) slides over rail rods 128 and 130 and moves longitudinally towards second compartment 112. Similarly, when threaded driving rod 125 is rotated by stepping motor 122 in the opposite direction, magnet carrier base 140 slides over rail rods 128 and 130 and moves towards wall 190 (i.e. away from the second compartment 112). Rail rods 128 and 130 prevent magnet carrier base 140 from being skewed or tilted to one side or the other, by the forces exerted by the rotation of threaded driving rod 125 during travel.

Figure 3L:
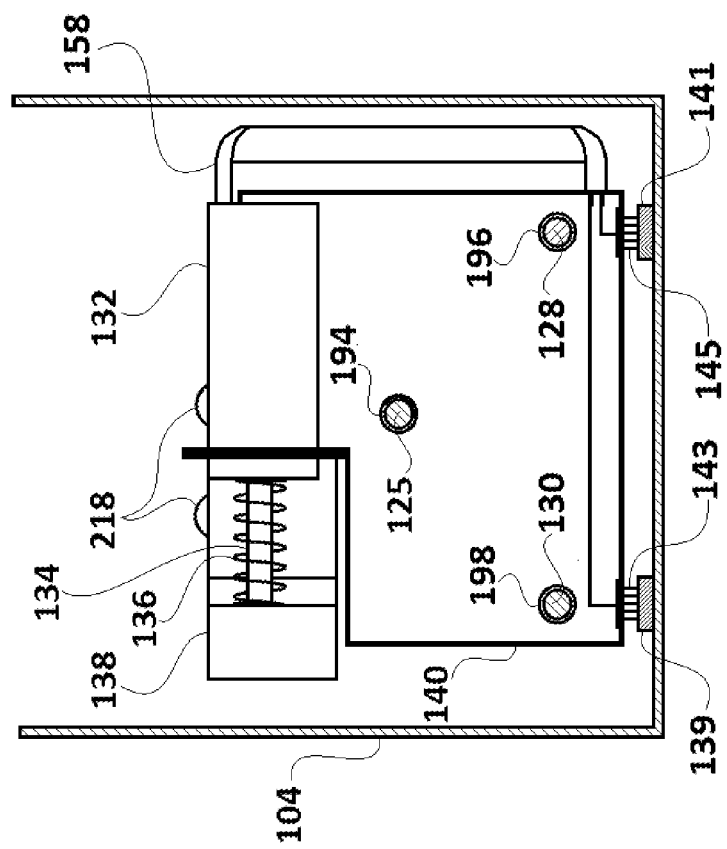
FIG. 3L is a cross-sectional view of an embodiment of a device similar to that shown in FIGS. 2A and 2B, where the view of this embodiment is of the same portion of the device as that taken along the lines F-F' in FIG. 2B.
Figure 3M:
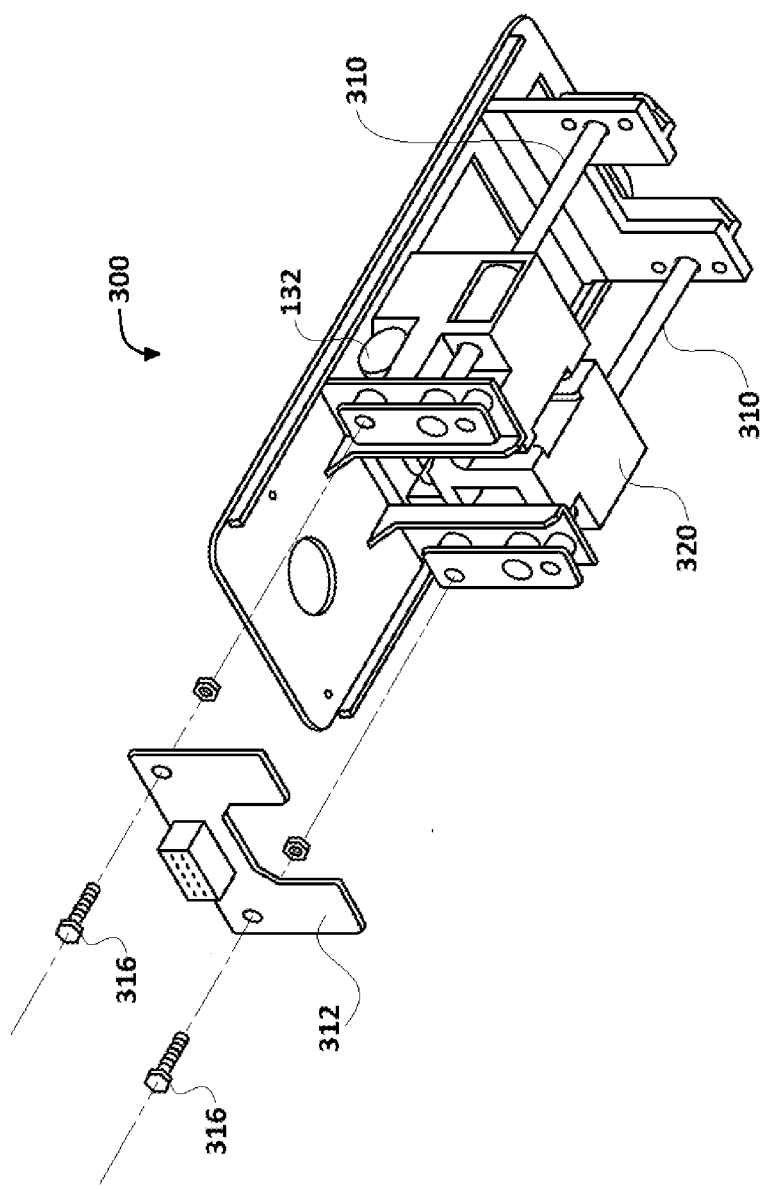
FIG. 3M is perspective, partially exploded view from below of a modified embodiment of a portion of the device in FIGS. 2A and 2B.

Another embodiment 300 of the rail support assembly for a magnet carrier base 320 is shown in FIGS. 3M and 3N. Circuit board 312 is bolted with bolts 316 to one of the struts supporting rods 310. Magnet carrier base 320, which includes solenoid 314 and magnet holder 138 (not shown), rides on rods 310 which pass through it as shown, and its movement along rods 310 can be powered by a stepping motor as described for moving magnet carrier base 140. Electrical power is supplied from circuit board 312 to solenoid 314 via rods 310 and internal brushes.

The assay device 100 and all components including microcomputer 107 are preferably powered by through an AC-to-DC converter (not shown), which connects to DC input port 81. The AC-to-DC converter receives AC power supply from domestic AC power source (for example, 110V, 60 Hz AC in the USA) through a power cord and provides a reduced or 12V DC supply at its output ports.

It is noted that though the present embodiment is powered by 12V DC supply, some embodiments of the invention may be powered with different DC voltages based on installed circuitry and components, or by DC batteries. Still further, for those embodiments of the invention which obtain DC supply by conversion of an AC power supply, the electrical circuitry for AC-DC conversion can be tailored in accordance with the type of AC power supply available at the location of usage and the desired magnitude of DC supply. For example, if an embodiment of the invention were to be used in the USA, the electrical circuitry for AC-DC conversion can be tailored in accordance with an available type of AC power supply of 110V-60 Hz, to achieve the desired magnitude of DC supply. For use in India, the electrical circuitry for AC-DC conversion can be tailored in accordance with an available type of AC power supply of 230V-50 Hz, and the desired magnitude of DC supply. Hence, all modifications in the circuitry of the device, or other modifications, to provide a desired level of DC supply from an available parent power source (such as AC power supply or battery/ies) are within the scope of the invention.

Stepping motor 122 is powered by connecting first output port 176 and second output port 178 of circuit board 174 to power supply ports 204 and 206 of stepping motor 122, respectively, using wires 148 and 150, respectively. Circuit board 174 is connected with main circuit board 117 through cord 105. Port 208 connects stepping motor 122 to ground through wire 152, and also connects to wire 156 (which connects port 188 to rail rod 130). The actuation of all ports on circuit board 174: port 176 and 178 which control stepping motor 122 and ports 188 and 180 which control current flow to ribbon 158 (FIG. 2A) or rail rods 130 and 128, respectively (FIG. 2B), are controlled by microcomputer 107, and each can be kept either in disabled or enabled state by microcomputer 107.

To drive stepping motor 122, either of ports 176 or 178 are enabled by microcomputer 107, providing power to inputs 204 or 206. Providing power to port 204 (while keeping port 206 disabled), powers stepping motor 122 to rotate driving shaft 124 in a first direction. When power is supplied to port 206 (keeping port 204 disabled), motor 122 is powered to rotate driving shaft 124 in the opposite direction. Any rotation of driving shaft 124 in either direction would also drive threaded driving rod 125 the same way. In the current embodiment, the enabling of either of ports 176 or 178 (and thus, powering of ports 204 or 206) leads to a potential difference of 9V DC with respect to port 208.

As noted, port 180 of the connector 142 is either connected to solenoid 132 through ribbon cord 158 (FIG. 2A) or, in FIG. 2B, is connected with first rail rod 128 through insulated conductor wire 154. The operation of the port 180 is also controlled by microcomputer 107. Port 180 can either be kept disabled or can be enabled at various DC voltage levels (preferably ranging between 2-9V) by microcomputer 107. Based on the DC voltage level provided by microcomputer 107 at port 180, an electric potential difference, preferably varying between 2-9 V DC, can be developed across outputs of ribbon wire 158 (FIG. 2A), or across first rail rod 128 and the second rail rod 130 (FIG. 2B). The first rail rod 128 and second rail rod 130 are further connected to an inputs 210 and 212 of solenoid 132 through insulated ribbon wire 158 (FIG. 2B), which is in turn connected to rods 128 and 130 through brushes 129, 131 and wires 135, 137, respectively. (FIGS. 3J and 3K). As noted, FIG. 3L shows another embodiment where solenoid 132 is connected with longitudinal strips 139, 141 which are connected through brushes 143, 145 and wires, to ribbon connector 158. The enabling of the embodiment of FIG. 3L is analogous to the other embodiments described above.

Input ports 210 and 212 are connected to ends of an electromagnet coil (not illustrated) included in solenoid 132. In an unenergized state of the electromagnet coil (or when port 180 is kept disabled by microcomputer 107), one end of solenoid shaft 134 lies within the solenoid 132. The other end of solenoid shaft 134 lies exterior to solenoid 132 and is connected to magnet holder 138. The solenoid shaft 134 can made of a ferromagnetic magnetic material (such as iron). A compressible spring 136 surrounds the length of the solenoid shaft 134 lying exterior to the solenoid 132. As illustrated, the compressible spring 136 is placed between solenoid 132 and magnet holder 138. Solenoid shaft 134 is movable longitudinally along its axis (which is perpendicular to axis 192, once solenoid 132 is enabled.

Figure 4A:
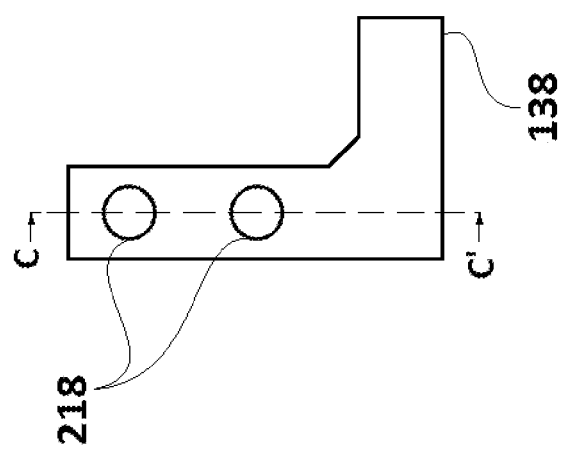
FIG. 4A is a plan view of the magnet carrier base of FIGS. 2A,2B and 3J.
Figure 4C:
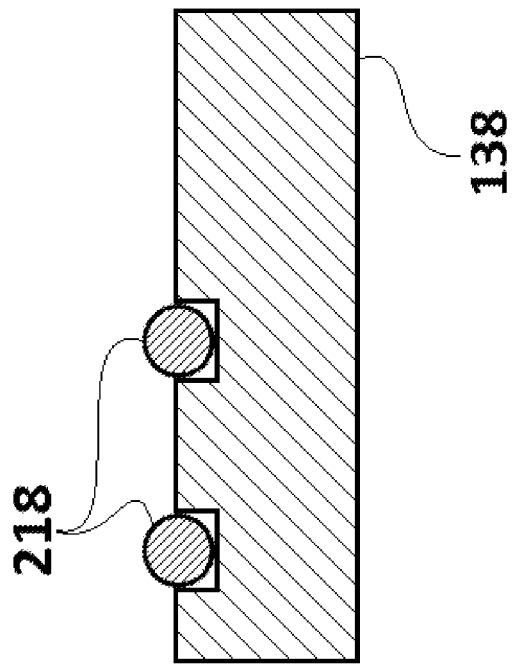
FIG. 4C is a cross-sectional view of another embodiment of the magnet carrier base of FIG. 4B.
Figure 4B:
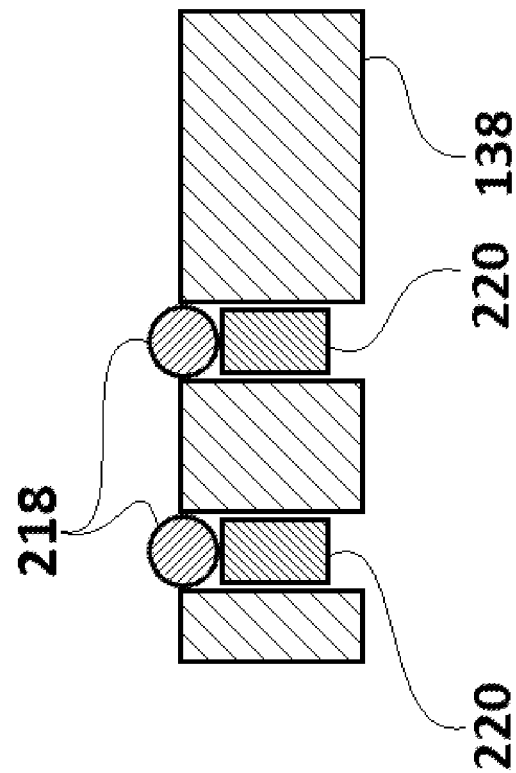
FIG. 4B is a cross-sectional view of one embodiment of the magnet carrier base of FIG. 4A, taken along line C-C'.

As illustrated in FIGS. 4A, 4B and 4C, magnet holder 138 includes two identical spherical scanning magnets 218, and may also include two cylindrical orienting magnets 220 (FIG. 4B). Each orienting magnet 220 is placed vertically in alignment below its corresponding scanning magnet 218. Orienting magnets 220 help align the poles of scanning magnets 218 in the same direction as the poles of orienting magnets 220. The magnet holder 138 is preferably made of a polymer (such as high-density polyethylene ("HDPE")). Each scanning magnet 218 (and corresponding orienting magnet 220 of FIG. 4B) is held in a well provided on the upper surface of magnet holder 138.

Microcomputer 107 can vary the voltage at port 180 and thus the amount of attractive force exerted by solenoid 132, to induce varying degrees of electromagnetic force pulling shaft 134 into solenoid 132. On being energized by flow of DC current through its coil by application of potential difference across rods 128 and 130 (FIG. 2B), or, as in FIG. 2A, across the leads of ribbon 158 (i.e. by enabling third output port 180 at a voltage levels between 2-9V), the electromagnetic force generated by solenoid 132 pulls varying length of the solenoid shaft 134 into the solenoid 132. As the solenoid shaft 134 is pulled into the solenoid 132, the magnet holder 138 moves closer to the solenoid 132 and the spring 136 gets compressed. On removal or lowering of the potential difference applied across rods 128 and 130 or the leads of ribbon 158 (done by disabling or lowering the voltage at third output port 180, and hence lowering of electric current through the solenoid 132) spring 136 releases and pushes magnet holder 138 away from the solenoid 132, thus pushing out the solenoid shaft 134, whereby it returns to its default position. Scanning platform 106 is positioned on the scanning box 102 immediately above magnet holder 138. In alternate embodiment 300 shown in FIGS. 3M and 3N, movement of magnet holder 138 within magnet carrier base 320 is achieved in a similar manner.

The two-dimensional space covered by magnet holder 138 as it moves along axis 192 and perpendicular axis 216 (the axis of shaft 134) is sufficiently large so that the magnet holder 138 can be moved under the scanning platform 106 over most of the surface of assay cartridge 10 (which rests on scanning platform 106). The dimensions of the driving box 104 and all components included within are chosen suitably to facilitate such two-dimensional movement of magnet holder 138.

Based on the type of assay performed and the type of assay cartridge 10 being scanned, the microcomputer 107 can be programmed/instructed to guide movement of magnet carrier base 140 along axis 192, and periodically, solenoid 132 is actuated to move magnet holder 138 back and forth.

An embodiment of assay cartridge 10 is shown in FIGS. 5A-6F. Assay cartridge 10 is preferably made of a transparent polystyrene, polytetrafluoroethylene ("Teflon®") or polyethylene, and has two rows of a series of wells, with the first well in each row labeled as 12 and 13, respectively, and the remaining wells in one row designated 14, and the remaining wells in the other row designated 15. Each well (12, 13, 14, 15) also has a mini-hole 16 (and one well 15 has a larger hole 19) which extends through the cartridge 10, as best seen in FIGS. 5D, 5E. Assay cartridge 10 also has a series of channels 18, which extend completely through the cartridge 10, and separate each well (12, 13, 14, 15) from the well next to it. As shown in FIGS. 6A to 6C, a transparent or translucent layer 20 (preferably a translucent plastic paraffin film, including but not limited to Parafilm® and similar products, which are transparent or translucent and can adhere to cartridge 10) covers and seals the wells (12, 13, 14, 15). Layer 20 adheres to the portions of cartridge base 10 between the wells (12, 13, 14, 15) and channels 18, to seal the contents of the wells (12, 13, 14, 15), and to seal one side of the channels 18 from the surroundings. Cover 22, as illustrated in FIGS. 6A-6D and 6F, is designed to protect layer 20, especially during transport, and is preferably made of paper or a polymer. The covering layer 22 also carries a QR code, other readable code, or a barcode 11 (provided on the surface of the cover 22 which is laid over layer 20). The barcode 11 (or other code) provides a unique identification code for assay cartridge 10. It is to be noted that in some embodiments, instead of being on the cover 22, the barcode 11 may be provided on the layer 20, or directly upon assay cartridge 10.

In one example of an Enzyme-Linked ImmunoSorbent Assay (ELISA) run with assay driver 100, sample solution is introduced into the well adjacent to well 13 (through hole 19) and a control solution is introduced into the well adjacent to well 12. Magnetic beads coated with antibody against antigens in the control solution (and which may target antigens in the sample, if the sample is positive) are also placed into wells 12 and 13.

In an alternative embodiment, the coated magnetic beads may be placed into the well 14 which is immediately adjacent to well 12 (containing control solution) and also into the well 15 which has hole 19 and which is immediately adjacent to well 13 (containing sample solution). From there, during an initial step in the assay, the magnetic beads are moved back into wells 12 and 13, respectively, to respectively contact sample and control solutions. The magnetic beads are then moved through the adjacent wells 14 and 15, respectively, before being moved to the remaining wells, serially. This added movement step can aid in washing of the magnetic beads after contacting samples and control solution and before contacting reagents for the other steps of the assay. In this embodiment, hole 19 would be located in well 13 instead of well 15.

Reagents for other steps in the assay (e.g., solutions of labeled detection antibodies which target and bind to the antigens; solutions to develop the labels on the detection antibodies into discernable colors) are loaded through mini-holes 16 of other wells 14 and 15. These reagents are placed in wells 14 and 15 in a series such that the requisite assay steps are performed as the magnetic beads are moved from wells 12 and 13 and through the series of wells 14 and 15. In an alternative embodiment, unlabeled detection antibodies mixed with labeled secondary antibodies may be used in place of labeled detection antibodies.

Prior to using cartridge 10 in an assay, the barcode 11 is scanned (can be by the scanner included in the scanning box 108 or can be done manually by the user) and the scanned barcode information is sent to a server/website, which identifies the assay type and provides the instructions about the assay steps and their timing (preferably over the Internet) to microcomputer 107 (preferably through a transceiver). Alternatively, the instructions can be retrieved from the server/website and manually input or electronically fed into microcomputer 107.

Cartridge 10 is inverted and placed on scanning platform 106, with the sealed side, i.e., the layer 22 side, facing down (see FIGS. 6A and 6B). From there, the components in driving box 104 are actuated by the instructions from microcomputer 107 to perform the assay steps in the correct sequence. For example, stepping motor 122 is actuated for sufficient time to drive movement of magnet holder 138 such that scanning magnets 218 move from their first position (directly below each of wells 12 and 13, or below adjacent wells 14, 15) to a position below the next wells 14, 15 (or 12, 13) in the series—and then to a position below the wells 14, 15 in the series which each contain a solution of labeled detection antibodies. Magnetic beads in the wells are thereby dragged by magnetic attraction to scanning magnets 218 along the inner side of layer 20 through the nearest channel 18, and into the respective next well in the series.

Optionally, solenoid 132 can be alternately actuated and de-energized to move magnet holder 138 back and forth to mix the magnetic beads with the solutions in wells 12, 13, 14, 15, any time mixing of well contents and beads is desired. During the mixing sequence, solenoid 132 may be held in the actuated or de-energized position for a defined period (approximately 1 or 2 seconds) to allow the magnetic beads to re-form a cluster. Rather than spring 136, another type of passive return mechanism, including an elastic band, may be used to return holder 138 to its resting position, before another potential is applied. Another coil could also be used to effect such return.

Stepping motor 122 is next actuated for sufficient time to drive movement of magnet carrier base 140 such that scanning magnets 218 move to a position below the last wells 14, 15 in the series—which each contain a development solution for the label. A well 15 with the development solution should develop color after magnetic beads arrive therein (because it is the control assay), and the well in row 14 with the development solution should develop a variable amount of color depending on the amount of analyte present in the sample. Movement of magnet carrier base 140 may also be actuated again, to carry magnetic beads to a previous well 14, 15 in the series so that the beads do not interfere with the optical reading of the developing solution.

In selecting scanning magnets 218 and orienting magnets 220, and the manner of movement of holder 138, important parameters include:
1. The ability to focus the magnetic field to produce a tight cluster of magnetic beads, so that during the assay (see below), the beads move cleanly through the air gaps in channels 18 without excessive scraping against the walls of channels 18.
2. Induce a magnetic field of sufficient strength to pull the magnetic beads when the magnets 218 are moved suddenly back and forth or otherwise to mix the beads with the well reagents, and also to pull the beads in a cluster cleanly through the channel.
3. The strength of the magnetic field acting on magnetic beads should be at a level that allows the bead cluster to spread out a bit (like a comet tail) when the magnetic field moves suddenly, so as to enhance mixing. The magnetic field strength should also be below a level where it would cluster the beads too tightly, cause interference with other magnets/channels, or cause interference with the circuit board (which may be part of the assay driver system). In one embodiment, a neodynium permanent magnet of Br-max of approximately 4500 Gauss may be used.
4. There must be a precise gap between the magnets and the layer 20 (on which beads rest). This is needed in order to produce a known motion patterns for the beads. The position of orienting magnets 220 can be adjusted vertically within magnet holder 138 to enable precise control over the clearance between magnets 218 and the layer 20.

The next step is scanning of the wells 14 and 15 which show color, to confirm the assay is functioning properly (specific wells 15 show color change), and if there was a positive result (based on whether the specific wells 14 shows color change). A sensor which reads overall light intensity (and/or with color filters) may be used to show the chemiluminescence or color change.

The relative antigen concentration in the sample may also be determined, based on the degree of color change. Preferably, the sensor results or the scanned images are captured through scanners 97 (FIGS. 3G, 3H), and are transmitted to the server/website for interpretation through unit 109 (FIGS. 1A, 1B), and/or to another authorized recipient or health care provider, and/or to the patient. The scanning and transmission of the sensor results or image can be automatically performed on the assay cartridge 10 by inverting it (so the well contents are visible from above) on scanning platform 106, in accordance with instructions provided to microcomputer 107. Alternatively, a scanner or results sensor can be separated from driver 100, and image scanning can be performed outside of driver 100.

The assay cartridge 10 described herein is preferably for use with assay driver 100, which actuates and controls performance of the assay, and reports results, in a secure remotely authorized system, as described herein. After assay completion, images scanned and representing the assay results are transmitted for interpretation or to the assay subject or his/her designees (including distribution to anyone who can receive the material under applicable HIPAA regulations).

Figure 7:
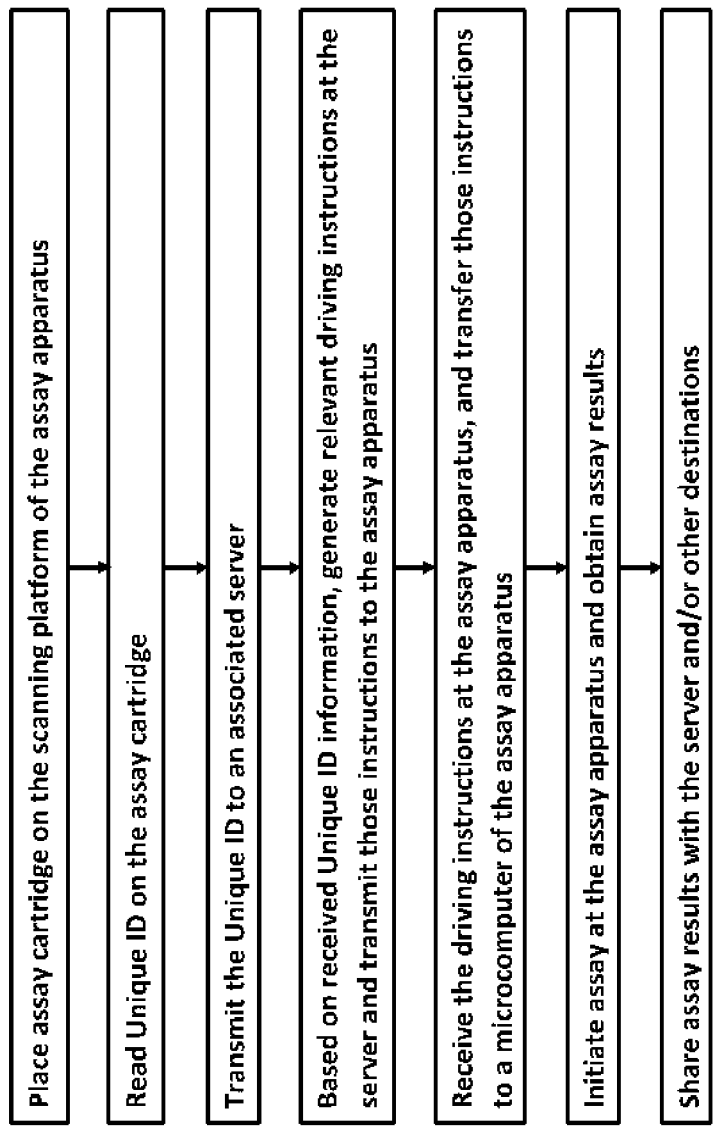
FIG. 7 is a flow diagram of the steps involved in initiating and performing an assay with the assay driving apparatus and the assay cartridge shown and described herein.
Figure 8:
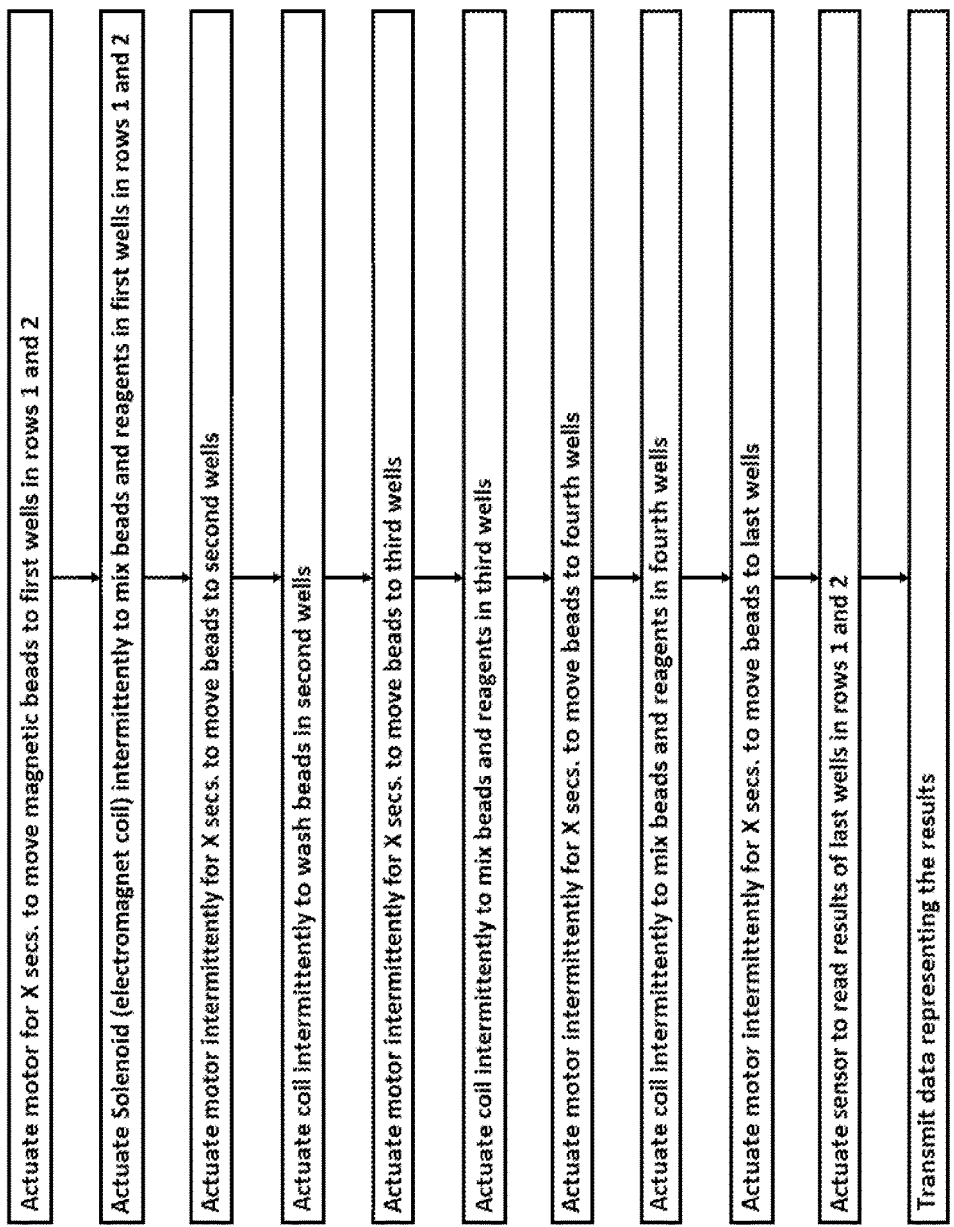
FIG. 8 is a flow diagram of the instructions for initiating and performing an assay with the assay driving apparatus and the assay cartridge shown and described herein.

A flow chart showing the steps of cartridge identification through assay imaging and transmission is shown in FIG. 7. A flow chart exemplifying the instructions executed by microcomputer 107 is shown in FIG. 8. The steps in FIG. 7 of transmitting the barcode and transmitting instructions can be wireless, through phone lines, or through the internet, or by any other means. The assay steps described above and the reagents and beads in various wells would be different in different assays and assay formats. The device 100 and system described herein is appropriate for use with any assay where magnetic beads can be used.

Example 1: Performing an ELISA Immunoassay

Cartridge 10 is loaded with antibody-coated magnetic beads and reagents suitable for an ELISA, and sample is added to the well adjacent to well 13, and a control is added to the well adjacent to well 12. The instructions are executed to induce assay driver to move magnet carrier base 140, containing magnet holder 138, such that the antibody-coated beads are moved through channels 18 and to the next well 14, 15, respectively. The antibody coating on the beads binds to reactive antigens in the sample or control which reactive antigens are then carried by the beads.

Oscillating movement of magnet holder 138 in a direction the same, different or transverse to the first axis induces mixing of beads with the contents of the wells in which they reside. The mixing can be carried out in certain wells, or in all wells in the series.

It is preferred that the strength of the magnetic field acting on magnetic beads, the acceleration and deceleration of holder 138, the distance of travel of holder 138, and the delay time between movements of holder 138 are adjusted so that the beads spread out somewhat (like a comet tail) when oscillating holder 138 to mix beads with the well contents. Optimization of the movement parameters of holder 138 to achieve rapid mixing of beads and well contents is therefore preferred.

The next wells 14, 15, in the series are loaded with detection antibodies carrying enzyme, or with unlabeled detection antibodies and secondary antibodies carrying enzyme. Ultimately, beads are moved to final wells 14, 15 containing the substrate for the enzyme carried by the detection or secondary antibodies, which induces a detectable color change. The color change can be accomplished with an enzyme-substrate combination. In such case, the wells where there is to be a color change may contain one of the following: PNPP (p-Nitrophenyl Phosphate), ABTS (2,2'-Azinobis [3-ethylbenzothiazoline-6-sulfonic acid]-diammonium salt), OPD (o-phenylenediamine dihydrochloride), or TMB (3,3',5,5'-tetramethylbenzidine)]. One suitable enzyme-substrate combination is horseradish peroxidase (HRP) as the enzyme and TMB as the detection substrate. When using chemiluminescent chemicals and HRP, which is another option, light is generated as well as a color change.

Some wells 14, 15 may optionally serve as wash chambers to separate the magnetic beads from reagents not bound to the beads—although this separation is also achieved by passage of the magnetic bead clusters through the air gaps in channels 18. Oscillating movement of magnet holder 138 in a direction transverse to the first axis induces mixing of beads with the contents of wells which contain wash reagents—when the beads reside in those wells.

In a sandwich-type ELISA, the concentration of analyte in sample or control solution is proportional to the amount of the analyte that gets attached to the antibody-coated magnetic particles, which in turn is proportional to the number of detection antibody molecules that get attached to the analyte. Because the detection or secondary antibodies are attached to HRP, the quantity of detection or secondary antibodies bound to the analyte governs the rate of catalytic conversion of TMB.

After a suitable reaction time (for example, 2-10 minutes) the color intensity can be quantified with a light source and detector, for example. The final wells can have results recorded or be scanned and imaged, and the image or results can be transmitted for remote analysis of the assay results, or to the patient or a designated recipient, as described further below. A suitable scanner for generating the assay well readings is a four-channel photoelectric color sensor, capable of sensing the total light signal and up to three color-filtered signals.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An apparatus for performing an assay where magnetic beads are moved through a plurality of wells which contain assay reagents, comprising:
    a substantially planar assay cartridge having a plurality of wells which are indentations in a first substantially planar surface of said cartridge, and said wells are separated and are connected by channels running between wells;
    at least one scanning magnet positioned to attract one or more sets of magnetic beads in the wells and move them with movement of the scanning magnet,
    a motor configured to move the at least one scanning magnet with respect to the assay cartridge along a first axis;
    a coil configured to actuate and de-actuate to oscillate said at least one scanning magnet along a second axis, wherein said first axis intersects the second axis.

2. The apparatus of claim 1, wherein the at least one scanning magnet is held in a magnet holder which is held by a base, and wherein the magnet holder is moveable with respect to the base along the second axis.

3. The apparatus of claim 2 further including rods which extend into the base and the base slides in the direction of the first axis along the rods.

4. The apparatus of claim 3 wherein the rods connect the coil to a power source.

5. The apparatus of claim 4, wherein the electrical potential of one rod is higher than the electrical potential of another rod.

6. The apparatus of claim 3, wherein movement of said at least one scanning magnet along the first axis is powered by rotation of an externally threaded shaft parallel to the first axis and extending through a mating threaded portion of the base.

7. The apparatus of claim 6, wherein the power source supplies DC to the rods and motor but the power source is connected with an AC initial source.

8. The apparatus of claim 6, wherein the motor is a stepping motor and the stepping motor is configured to power the rotation of the externally threaded shaft.

9. The apparatus of claim 8, further including a microcomputer which controls intervals of rotation of the stepping motor.

10. The apparatus of claim 9, wherein the microcomputer also controls current flow to the rods, which are connected to a power source, and actuation of the coil.

11. The apparatus of claim 10, wherein the microcomputer is connected to the rods, which are connected to the coil through wires or a combination of wires and brushes.

12. The apparatus of claim 2, wherein a shaft or an armature resides inside the coil, and actuation of the coil moves the shaft or armature, which in turn moves the magnet holder along the second axis.

13. The apparatus of claim 1 wherein a power source is connected with the coil through brushes, wires or a combination of the two.

14. The apparatus of claim 13, further including a microcomputer which controls current flow to the wires or brushes and actuation of the coil.

15. The apparatus of claim 14, wherein the microcomputer is connected with the coil through a combination of metallic strips which extend parallel to the first axis, brushes contacting the strips, and wiring connecting the brushes and the coil.

16. The apparatus of claim 1, wherein the coil includes a spring such that its decompression returns said at least one scanning magnet to its resting position when the coil is de-actuated.

17. The apparatus of claim 1, wherein the first axis is transverse to the second axis.

18. The apparatus of claim 1, wherein the assay cartridge has at least two parallel rows of wells and there are at least two scanning magnets.

19. The apparatus of claim 18, further including at least two orienting magnets, each positioned to magnetically interact with one of the scanning magnets.

20. The apparatus of claim 19, wherein the orienting magnets are substantially cylindrical.

21. The apparatus of claim 18, wherein the scanning magnets are substantially spherical.

22. The apparatus of claim 1, further including a scanner which can image or acquire sensor data from at least one well of the assay cartridge.

23. The apparatus of claim 22, further including a transmitter which can transmit said image or sensor data to a remote location.

24. An apparatus for performing an assay where magnetic beads are moved through a plurality of wells which contain assay reagents, comprising:
   a substantially planar assay cartridge having a plurality of wells which are indentations in a first substantially planar surface of said cartridge, and said wells are separated by channels;
   at least one scanning magnet held in a moveable base, to attract one or more sets of magnetic beads in the wells and move them with movement of the base,
   a motor configured to move the base with respect to the assay cartridge in the direction of a first axis along the rods, which extend into the base;
   a coil configured to actuate and de-actuate to oscillate said at least one scanning magnet along a second axis, wherein said first axis intersects the second axis.

25. An apparatus for performing an assay where magnetic beads are moved through a plurality of wells which contain assay reagents, comprising:
   a substantially planar assay cartridge having at least two parallel rows of wells which are indentations in a first substantially planar surface of said cartridge, and said wells are separated by channels;
   at least two scanning magnets positioned to attract one or more sets of magnetic beads in the parallel rows of wells and move them with movement of the scanning magnets,
   a motor configured to move the scanning magnets with respect to the assay cartridge along a first axis;
   a coil configured to actuate and de-actuate to oscillate said scanning magnets along a second axis, wherein said first axis intersects the second axis.

* * * * *